United States Patent
DeLuca et al.

(10) Patent No.: US 6,432,936 B1
(45) Date of Patent: Aug. 13, 2002

(54) CRYSTALLINE 1α-HYDROXYVITAMIN $D_2$ AND METHOD OF PURIFICATION THEREOF

(75) Inventors: Hector F. DeLuca, Deerfield; Rafal R. Sicinski, Madison; Hazel Holden, Fitchburg; James Brian Thoden, Madison, all of WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/233,738

(22) Filed: Jan. 20, 1999

(51) Int. Cl.[7] ................ A61K 31/592; C07C 401/00
(52) U.S. Cl. ........................ 514/167; 552/653
(58) Field of Search ............... 552/653; 514/167

(56) References Cited

U.S. PATENT DOCUMENTS

| | | | |
|---|---|---|---|
| 3,585,221 A | 6/1971 | DeLuca | 260/397.2 |
| 3,833,622 A | 9/1974 | Babcock et al. | 260/397.2 |
| 3,880,894 A | 4/1975 | DeLuca et al. | 260/397.2 |
| 3,907,843 A | 9/1975 | DeLuca et al. | 260/397.2 |
| 4,338,250 A | 7/1982 | DeLuca et al. | 260/397.2 |
| 4,505,906 A | 3/1985 | DeLuca et al. | 514/167 |
| 4,554,105 A * | 11/1985 | Hesse | 260/397.2 |
| 4,758,383 A * | 7/1988 | Tachibana | 260/397.2 |
| 5,266,712 A * | 11/1993 | Lanquetin | 552/574 |

FOREIGN PATENT DOCUMENTS

| | | | |
|---|---|---|---|
| EP | 0078704 | 5/1983 | |
| EP | 0078705 | 5/1983 | |
| EP | 0270867 | 6/1988 | |
| WO | 9208730 | * 5/1992 | C07J/1/00 |

OTHER PUBLICATIONS

Strungell et al. (DN 95374450, Medline, abstract of Biochemical Journal, (1995, 310 (pt 1), 233–41).*
Solvay Product Information, 1α–Hydroxyergocalciferol, Vitamin D Workship, Orlando, Florida, 1994.
Solvay Product Information, Ercalcidol, 10th Vitamin D Workshop, Strasbourg, France, May 24–29, 1997.
Solvay Product Information Bulletin and Certificate of Analysis, 1α–Hydroxyergocalciferol, May 6, 1998.
Moriarty et al, "Synthesis and Stereochemical Studies on 1α and 1β–Hydroxy Vitamin $D_2$", Eighth Workshop on Vitamin D, Abstracts, Jul. 5–10, 1991, Paris, France.
Calbiochem, Vitamin $D_2$, 1α–Hydroxy, Oct. 6, 1998.
Tachibana, A Convenient Synthesis of 1α–Hydroxyvitamin $D_2$, The Chemical Society of Japan, Nov., 1988, pp. 3915–3918.
Tachibana, Syntheses of 1β–Hydroxyvitamin $D_2$ and $D_3$, The Chemical Society of Japan, Jul. 30, 1988, pp. 2090–2092.

* cited by examiner

Primary Examiner—Sabiha Qazi
(74) Attorney, Agent, or Firm—Andrus, Sceales, Starke & Sawall, LLP

(57) ABSTRACT

A method of purifying 1α-hydroxyvitamin $D_2$ to obtain 1α-hydroxyvitamin $D_2$ in crystalline form. The method includes the steps of boiling a solvent selected from the group consisting of ethyl formate, ethyl acetate and a 2-propanol-hexane mixture under inert atmosphere, dissolving a product containing 1α-hydroxyvitamin $D_2$ to be purified in the. solvent, cooling the solvent and dissolved product below ambient temperature for a sufficient amount of time to form a precipitate of 1α-hydroxyvitamin $D_2$ crystals, and recovering the 1α-hydroxyvitamin $D_2$ crystals. Optionally, petroleum ether may be added to the solvent after dissolving the product to be purified in the solvent.

18 Claims, 18 Drawing Sheets

# CRYSTALLINE 1α-HYDROXYVITAMIN D₂ AND METHOD OF PURIFICATION THEREOF

STATEMENT REGARDING FEDERALLY SPONSORED RESEARCH OR DEVELOPMENT

This invention was made with United States Government support awarded by the National Institutes of Health (NIH), Grant #DK-14881. The United States Government has certain rights in this invention.

BACKGROUND AND SUMMARY OF THE INVENTION

The present invention relates to purification of organic compounds, and more particularly to the purification of 1α-hydroxyvitamin $D_2$ (1αOH-$D_2$) by preparing it in crystalline form.

Purification of organic compounds, especially those designated for pharmaceutical use, is of considerable importance for chemists synthesizing such compounds. Preparation of the compound usually requires many synthetic steps and, therefore, the final product can be contaminated not only with side-products derived from the last synthetic step of the procedure but also with compounds that were formed in previous steps. Even chromatographic purification, which is a very efficient but relatively time-consuming process, does not usually provide compounds which are sufficiently pure to be used as drugs.

Depending on the method used to synthesize 1α-hydroxyvitamin D compounds, different minor undesirable compounds can accompany the final product. Thus, for example, if direct C-1 hydroxylation of 5,6-trans geometric isomer of vitamin D is performed, followed by $SeO_2$/NMO oxidation and photochemical irradiation [see Andrews et al., *J. Org. Chem.* 51, 1635 (1986); Calverley et al., *Tetrahedron* 43, 4609 (1987); Choudry et al., *J. Org. Chem.* 58, 1496 (1993)], the final 1α-hydroxyvitamin D product can be contaminated with 1β-hydroxy- as well as 5,6-trans isomers. If the method consists of C-1 allylic oxidation of the 4-phenyl-1,2,4-triazoline-3,5-dione adduct of the previtamin D compound, followed by cycloreversion of the modified adduct under basic conditions [Nevinckx et al., *Tetrahedron* 47, 9419 (1991); Vanmaele et al., *Tetrahedron* 41, 141 (1985) and 40, 1179 (1991); Vanmaele et al., *Tetrahedron Lett.* 23, 995 (1982)], one can expect that the desired 1α-hydroxyvitamin can be contaminated with the previtamin 5(10),6,8-triene and 1β-hydroxy isomer. One of the most useful C-1 hydroxylation methods, of very broad scope and numerous applications, is the experimentally simple procedure elaborated by Paaren et al. [see *J Org. Chem.* 45, 3253 (1980) and *Proc. Natl. Acad. Sci. U.S.A.* 75, 2080 (1978)]. This method consists of allylic oxidation of 3,5-cyclovitamin D derivatives, readily obtained from the buffered solvolysis of vitamin D tosylates, with $SeO_2$/t-BuOOH and subsequent acid-catalyzed cycloreversion to the desired 1α-hydroxy compounds. Taking into account this synthetic path it is reasonable to assume that the final product can be contaminated with 1β-hydroxy epimer, 5,6-trans isomer and the previtamin D form. 1α-hydroxyvitamin $D_4$ is another undesirable contaminant found in 1α-hydroxyvitamin $D_2$ synthesized from vitamin $D_2$ or from ergosterol. 1α-hydroxyvitamin $D_4$ results from C-1 oxidation of vitamin $D_4$, which in turn is derived from contamination of the commercial ergosterol material. Typically, the final product may contain up to about 1.5% by weight 1α-hydroxyvitamin $D_4$. Thus, a purification technique that would eliminate or substantially reduce the amount of 1α-hydroxyvitamin $D_4$ in the final product to less than about 01.–0.2% would be highly desirable.

The vitamin D conjugated triene system is not only heat- and light-sensitive but it is also prone to oxidation, leading to the complex mixture of very polar compounds. Oxidation usually happens when a vitamin D compound has been stored for a prolonged time. Other types of processes that can lead to a partial decomposition of vitamin D compounds consist of the some water-elimination reactions; their driving force is allylic (1α-) and homoallylic (3β-) position of the hydroxy groups. The presence of such above-mentioned oxidation and elimination products can be easily detected by thin-layer chromatography. Thus, for example, using pre-coated aluminum silica sheets [with UV indicator; from EM Science (Cherry Hill, N.J.)] and solvent system hexane-ethyl acetate (4:6), the spot of 1α-OH-$D_2$($R_f$ 0.27) and its elimination products ($R_f$'s ca. 0.7–0.9) are visible in ultraviolet light. Also, after spraying with sulfuric acid and heating, an additional spot can be visualized ($R_f$ 0), derived from oxidation products.

Usually, all 1α-hydroxylation procedures require at least one chromatographic purification. However, even chromatographically purified 1α-hydroxyvitamin $D_2$, although showing consistent spectroscopic data, suggesting its homogeneity, does not meet the purity criteria required for therapeutic agents that can be orally, parenterally or transdermally administered. Therefore, it was evident that a suitable method of purification of 1α-hydroxyvitamin $D_2$ is required.

Since it is well known that the simplest procedure that can be used for compound purification is a crystallization process, it was decided to investigate purification of 1α-OH-$D_2$ by means of crystallization. The solvent plays a crucial role in the crystallization process, and is typically an individual liquid substance or a suitable mixture of different liquids. For crystallizing 1α-hydroxyvitamin $D_2$, the most appropriate solvent and/or solvent system is characterized by the following factors:

(1) low toxicity;
(2) low boiling point;
(3) significant dependence of solubility properties with regard to temperature (condition necessary for providing satisfactory crystallization yield); and
(4) relatively low cost.

It was found that highly apolar solvents (e.g. hydrocarbons) were not suitable due to the low solubility of 1α-OH-$D_2$ in them. Quite the reverse situation occurred in highly polar solvent media (e.g. alcohols), in which 1αOH-$D_2$ showed too high solubility. Therefore, it was concluded that for the successful crystallization of 1α-OH-$D_2$, a solvent of medium polarity is required or, alternatively, a solvent mixture consisting of two (or more) solvents differing considerably in polarity. Interestingly, hexane, so frequently used for crystallization purposes with co-solvents like acetone, ethyl acetate or diethyl ether, was found less suitable for crystallization of 1α-OH-$D_2$. Unusually low yields of crystallization were obtained when hexane-containing solvent systems were used. However, it was discovered that replacement of the hexane in such solvent mixtures with petroleum ether increased significantly the yield of crystals. After numerous experiments it was found that an individual solvent, namely ethyl formate, was most useful for the crystallization of 1α-OH-$D_2$. In addition, binary and ternary solvent systems namely: ethyl acetate-petroleum ether and 2-propanol-hexane-petroleum ether, respectively, also performed well. These solvents are all characterized by low toxicity, and they are very easy to remove by evaporation or other well known methods. In all cases the crystallization process occurred easily and efficiently; and the precipitated crystals were sufficiently large to assure their recovery by filtration.

DETAILED DESCRIPTION OF THE INVENTION

The present invention provides a valuable method of purification of 1α-hydroxyvitamin D$_2$, a pharmacologically important compound, characterized by the formula shown below:

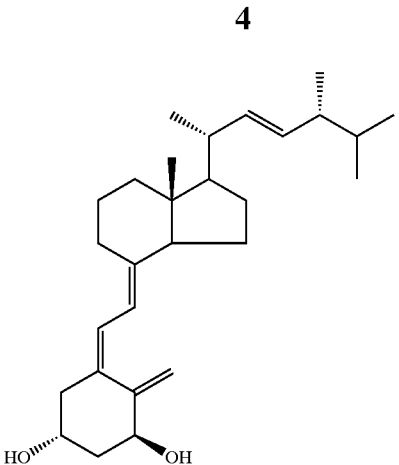

The purification technique involves obtaining the 1α-hydroxyvitamin D$_2$ product in crystalline form by utilizing a crystallization procedure wherein the 1α-hydroxyvitamin D$_2$ material to be purified is dissolved using as the solvent or solvent system one of the following:

(1) a single solvent system, namely, ethyl formate;
(2) a binary solvent system, namely, ethyl acetate and petroleum ether; or
(3) a ternary solvent system, namely, 2-propanol in combination with hexane and petroleum ether.

Thereafter, the solvent or solvent system can be removed by evaporation, with or without vacuum, or other means as is well known. The technique can be used to purify a wide range of final products containing 1α-hydroxyvitamin D$_2$ obtained from any known synthesis thereof, and in varying concentrations, i.e. from microgram amounts to kilogram amounts. As is well known to those skilled in this art, the amount of solvent utilized should be minimized and/or adjusted according to the amount of 1α-hydroxyvitamin D$_2$ to be purified.

Figure 5A:
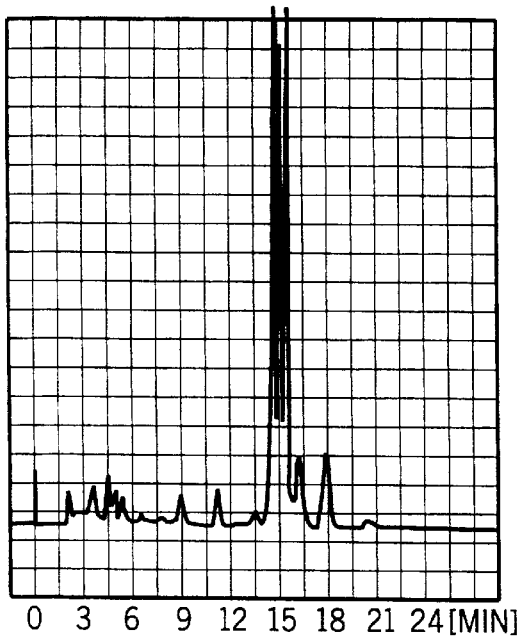
FIGS. 5a–5d are HPLC (4.6 mm×25 cm Zorbax-Eclipse XDB-C18 column, 7% water in methanol, 1.5 mL/min; UV detection at 260 nm) profiles of the solid 1α-hydroxyvitamin D$_2$ material before crystallization (FIG. 5a) and the crystals resulted after two crystallizations from: HCOOEt (FIG. 5b), AcOEt-petroleum ether (FIG. 5c) and iPrOH-hexane-petroleum ether (FIG. 5d). In the region indicated by asterisk (ca. 15 min) sensitivity was decreased 20 times.

The usefulness and advantages of the present crystallization procedures is shown in the following specific Examples. Solid 1α-hydroxyvitamin D$_2$ product, obtained by Paaren's, supra, method, purified by flash chromatography on silica, and stored for few months in refrigerator, was used as a suitable starting material. Although this material still showed reasonably good 500 MHz $^1$H NMR spectrum (FIGS. 1g, 1h), concomitant compounds were detected by straight- and reverse-phase HPLC (FIGS. 2a and 5a, respectively) and, moreover, the presence of some oxidation products was confirmed by TLC (presence of a spot at $R_f$ 0). After recrystallization from the solvents listed above, the precipitated material was observed under microscope to confirm its crystalline form (FIGS. 4a–4f). Additionally, in the case of crystals precipitated from methyl formate, X-ray diffraction analysis was performed. The corresponding crops of crystals were then carefully analyzed and their significantly improved purity was confirmed by straight-phase HPLC (FIGS. 2b, 2c, 2d), reverse-phase HPLC (FIGS. 5b, 5c, 5d), TLC and 500 MHz $^1$H NMR (FIGS. 1a–1f). Yields of crystallizations were high and the obtained crystals showed a relatively sharp melting point.

Figure 2A:
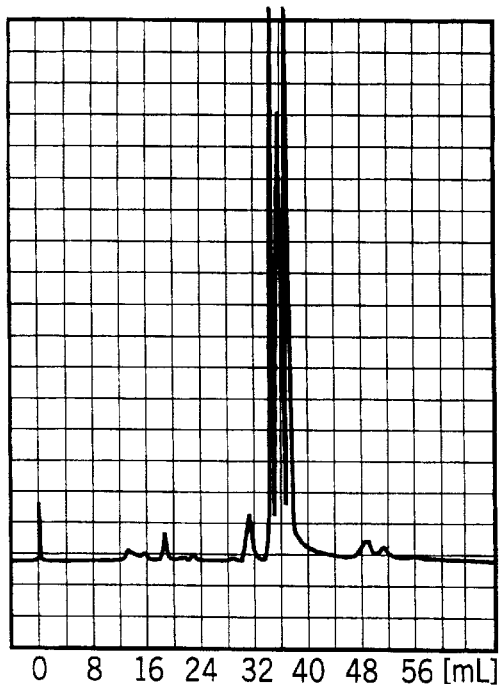
FIGS. 2a–2d are HPLC (10 mm×25 cm Zorbax-Sil column, 15% 2-propanol in hexane, 4 mL/min; UV detection at 260 nm) profiles of the solid 1α-hydroxyvitamin D$_2$ material before crystallization (FIG. 2a) and the crystals resulted after two crystallizations using the following solvent system: HCOOEt (FIG. 2b), AcOEt-petroleum ether (FIG. 2c) and iPrOH-hexane-petroleum ether (FIG. 2d). In the region indicated by the asterisk (ca. 36 mL) sensitivity was decreased 20 times.
Figure 2B:
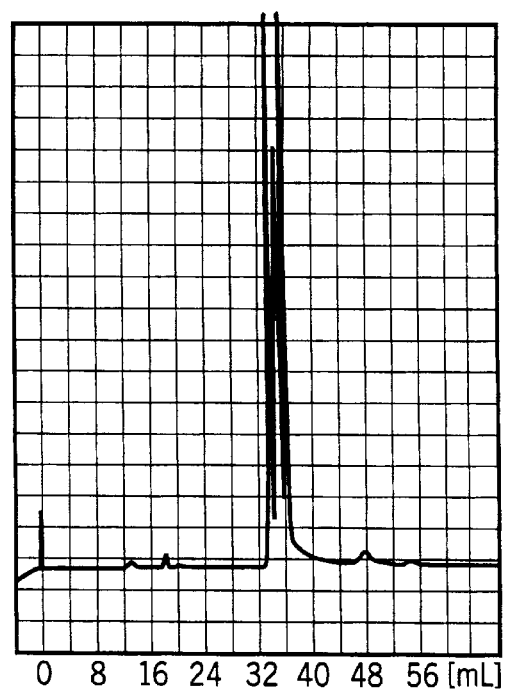
Figure 2C:
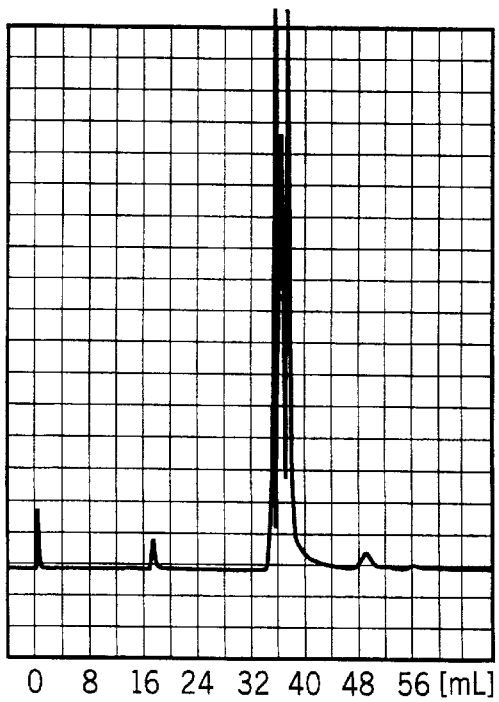

As it can be seen from FIGS. 2b and 2c, HPLC profiles of 1α-hydroxyvitamin D$_2$ obtained after two crystallizations from ester-containing solvents indicate presence of a small amount of less polar impurities (peaks at $R_v$ ca. 18 mL) which most likely originate from the corresponding 1α-OH-D$_2$ formate(s) and acetate(s) formed in minimal quantities in the equilibrium processes:

HCOOEt(CH3COOEt)+ROH⇌HCOOR(CH3COOR)+EtOH

However, the small amount of such esterificated compounds (less than 0.4%) presents no problem for pharmacological application of the crystalline vitamin $D_2$ compound due to the well-known fact that vitamin D esters undergo hydrolysis in living organisms.

Figure 5B:
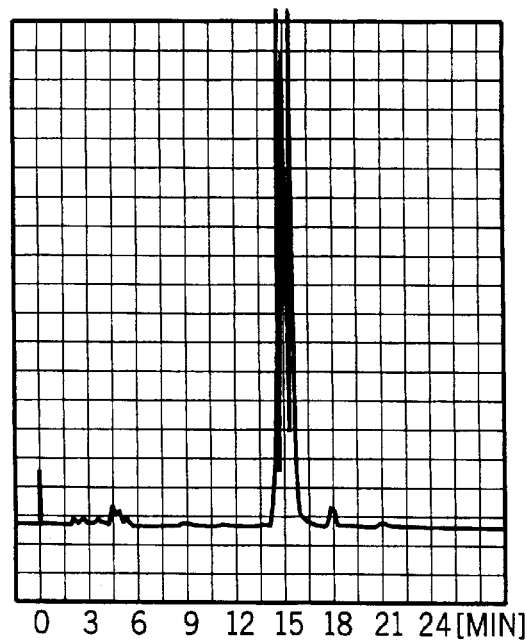
Figure 5C:
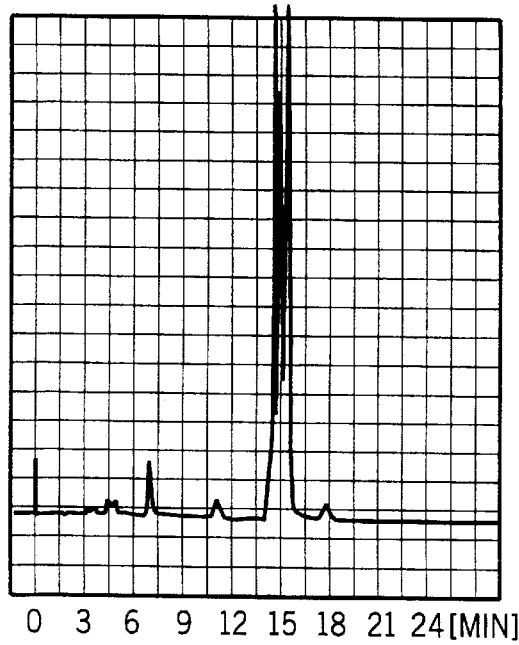
Figure 5D:
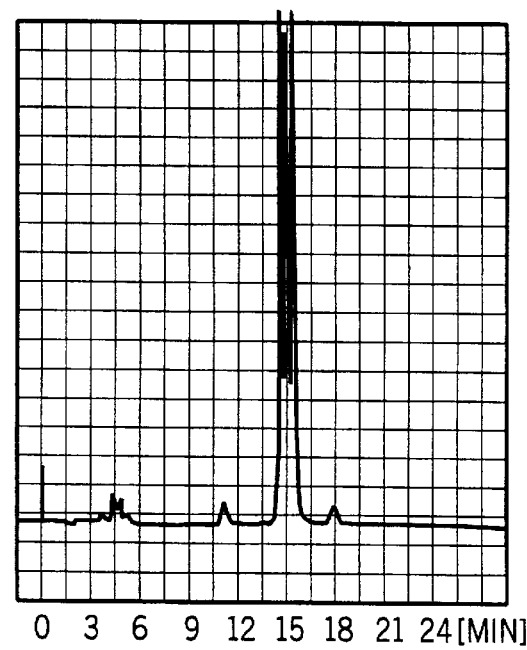
Figure 6A:
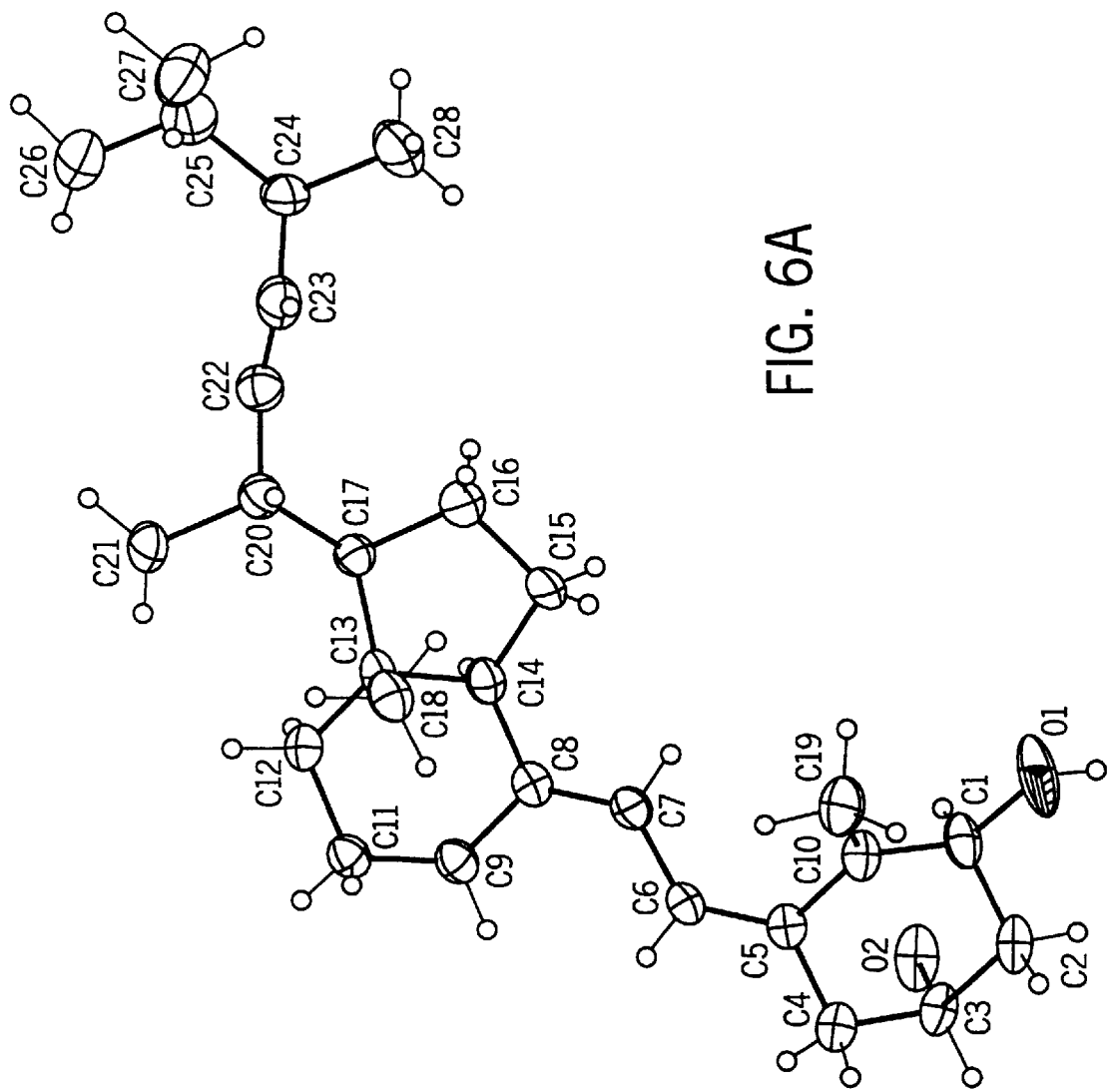
FIGS. 6a and 6b are illustrations of the three dimensional structure of 1α-hydroxyvitamin D$_2$ as defined by the atomic positional parameters discovered and set forth herein.
Figure 6B:
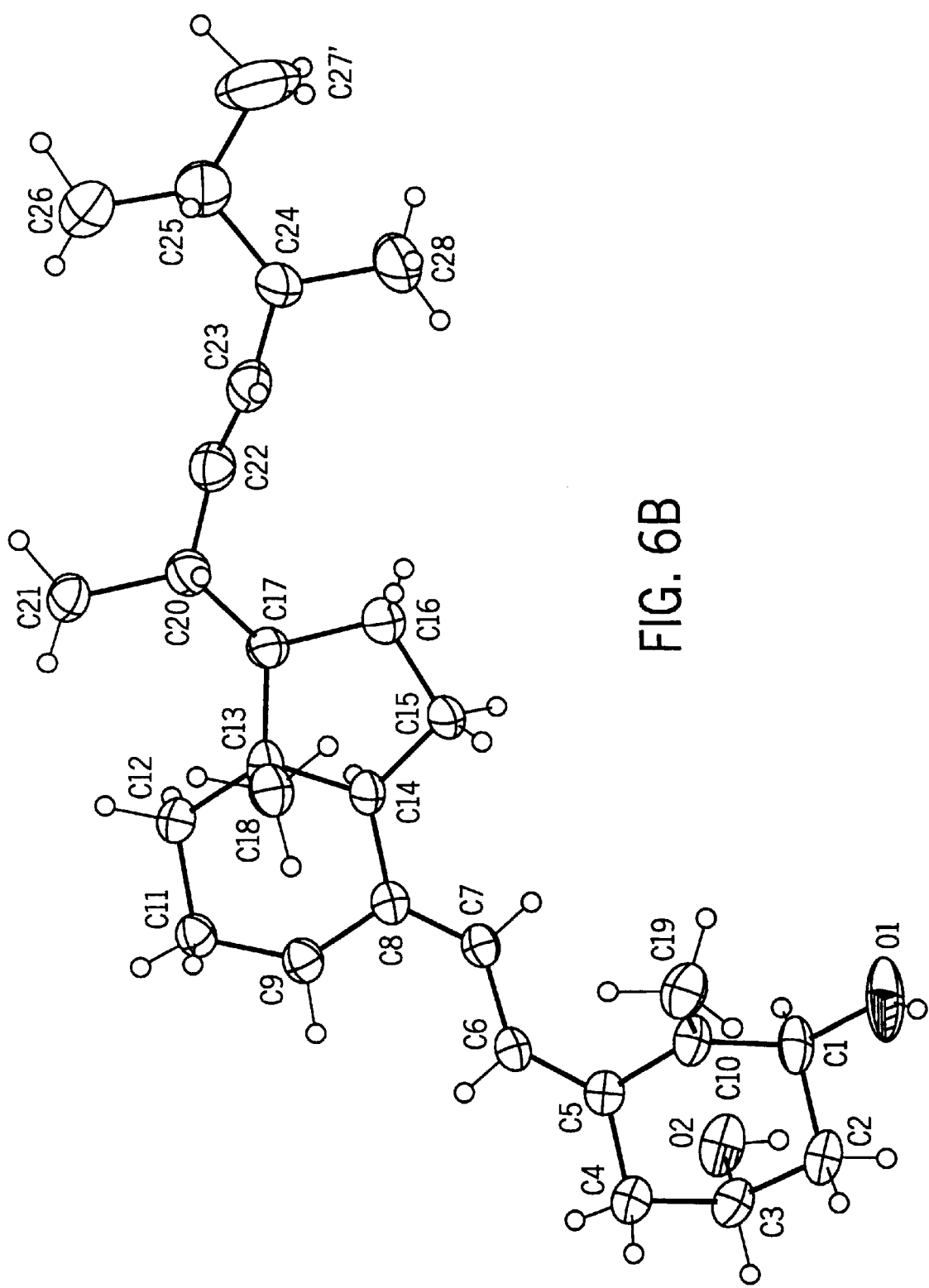

Also, the corresponding reverse-phase HPLC profiles of the recrystallized 1α-hydroxyvitamin $D_2$, shown in FIGS. 5b, 5c and 5d, clearly indicate a considerable improvement in the compound's purity. The important observation consists of the significantly diminished proportion of the concomitant 1α-hydroxyvitamin $D_4$ (peak of retention time ca. 18 mL) in the recrystallized compound. The content of this impurity has decreased more than 4 times (4.1–4.3) in respect to its value in the starting 1α-hydroxyvitamin $D_2$ product and does not exceed 0.2%.

The described crystallization processes of the synthetic 1α-hydroxyvitamin $D_2$ product represents a valuable purification method, which can remove not only some side products derived from the synthetic path, but, moreover, concomitant 1α-hydroxyvitamin $D_4$. Such impurity is the result of the contamination of natural ergosterol with its 22,23-dihydro analog and, consequently, vitamin $D_4$ is present in different proportions in the commercially available vitamin $D_2$. Column chromatography and straight-phase HPLC separation of 1α-hydroxyvitamin $D_4$ (formed after 1α-hydroxylation process) from 1α-hydroxyvitamin $D_2$ is practically impossible due to their similar chromatographical properties and larger-scale separation is also difficult by reverse-phase HPLC.

CRYSTALLIZATION OF 1α-HYDROXYVITAMIN $D_2$

EXAMPLE 1

Figure 3A:
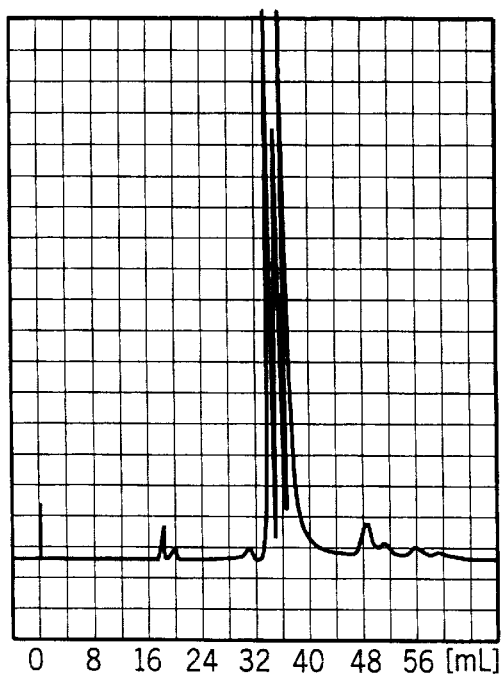
FIGS. 3a–3i are HPLC (10 mm×25 cm Zorbax-Sil column, 15% 2-propanol in hexane, 4 mL/min; UV detection at 260 nm) profiles of the crystals of 1α-hydroxyvitamin D$_2$ resulted after single crystallization using the following solvent system: HCOOEt (FIG. 3a), AcOEt-petroleum ether (FIG. 3d) and iPrOH-hexane-petroleum ether (FIG. 3g); the HPLC profiles of mother liquors after single crystallization using the following solvent systems: HCOOEt (FIG. 3b), AcOEt-petroleum ether (FIG. 3e) and iPrOH-hexane-petroleum ether (FIG. 3h); and the HPLC profiles of mother liquors after two crystallizations using the following solvent system: HCOOEt (FIG. 3c), AcOEt-petroleum ether (FIG. 3f) and iPrOH-hexane-petroleum ether (FIG. 3i). Region with decreased sensitivity (ca. 36 mL) is indicated by asterisk.
Figure 3B:
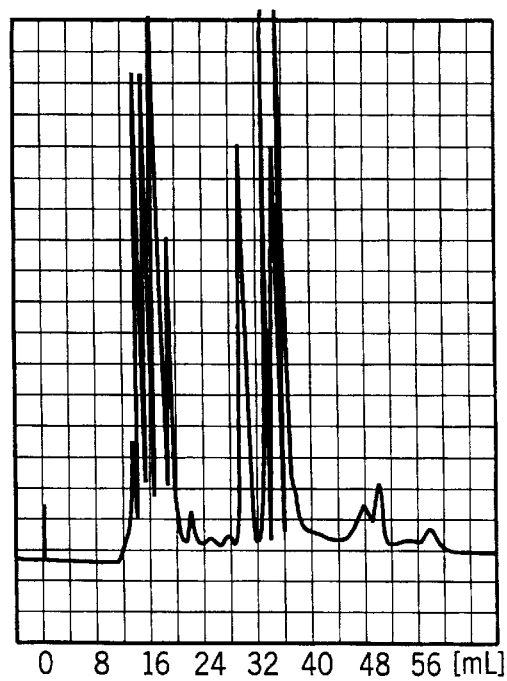

Crystallization from ethyl formate (a) 1α-Hydroxyvitamin $D_2$ product (50 mg) to be purified was dissolved in boiling ethyl formate (1.2 mL, Aldrich) under argon atmosphere, left at room temperature (68° F.) for a few hours (1–3 hrs) and then in a refrigerator (35–45° F.) overnight (8–12 hrs). The precipitated crystals were filtered off, washed with a small volume of a cold (0° C.) ethyl formate and dried. The yield of crystalline material was 38 mg (76%). HPLC profiles of crystals and mother liquor are shown in FIGS. 3a, 3b.

Figure 1A:
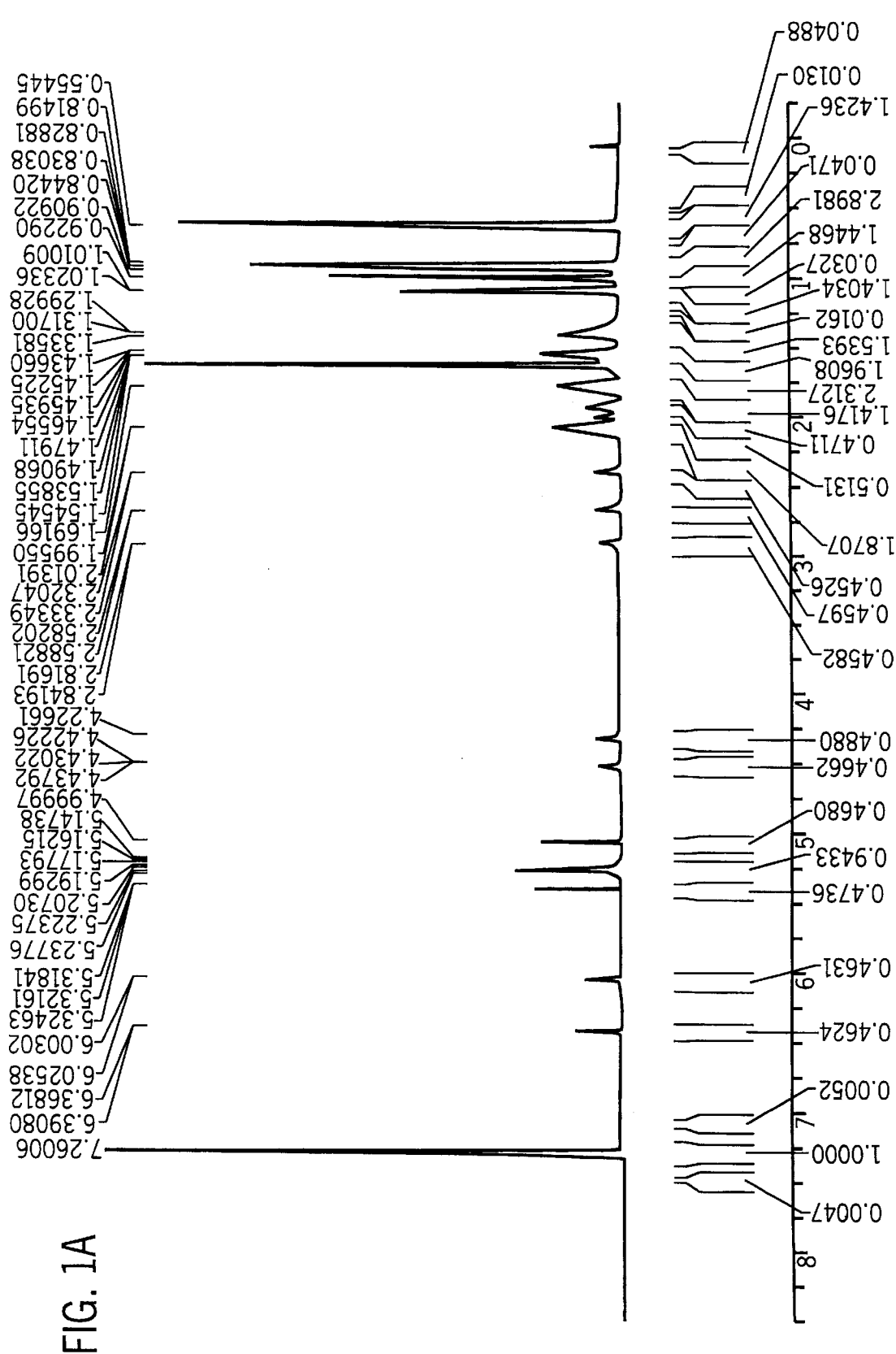
FIGS. 1a–1h are graphs of $^1$H NMR spectra (CDCl$_3$, 500 MHz) of the crystals of 1α-hydroxyvitamin D$_2$ resulted after two crystallizations using the following solvent system: HCOOEt (FIGS. 1a and 1b), AcOEt-petroleum ether (FIGS. 1c and 1d) and iPrOH-hexane-petroleum ether (FIGS. 1e and 1f) as well as the spectrum of the solid 1α-hydroxyvitamin D$_2$ material before crystallization (FIGS. 1g and 1h)
Figure 1B:
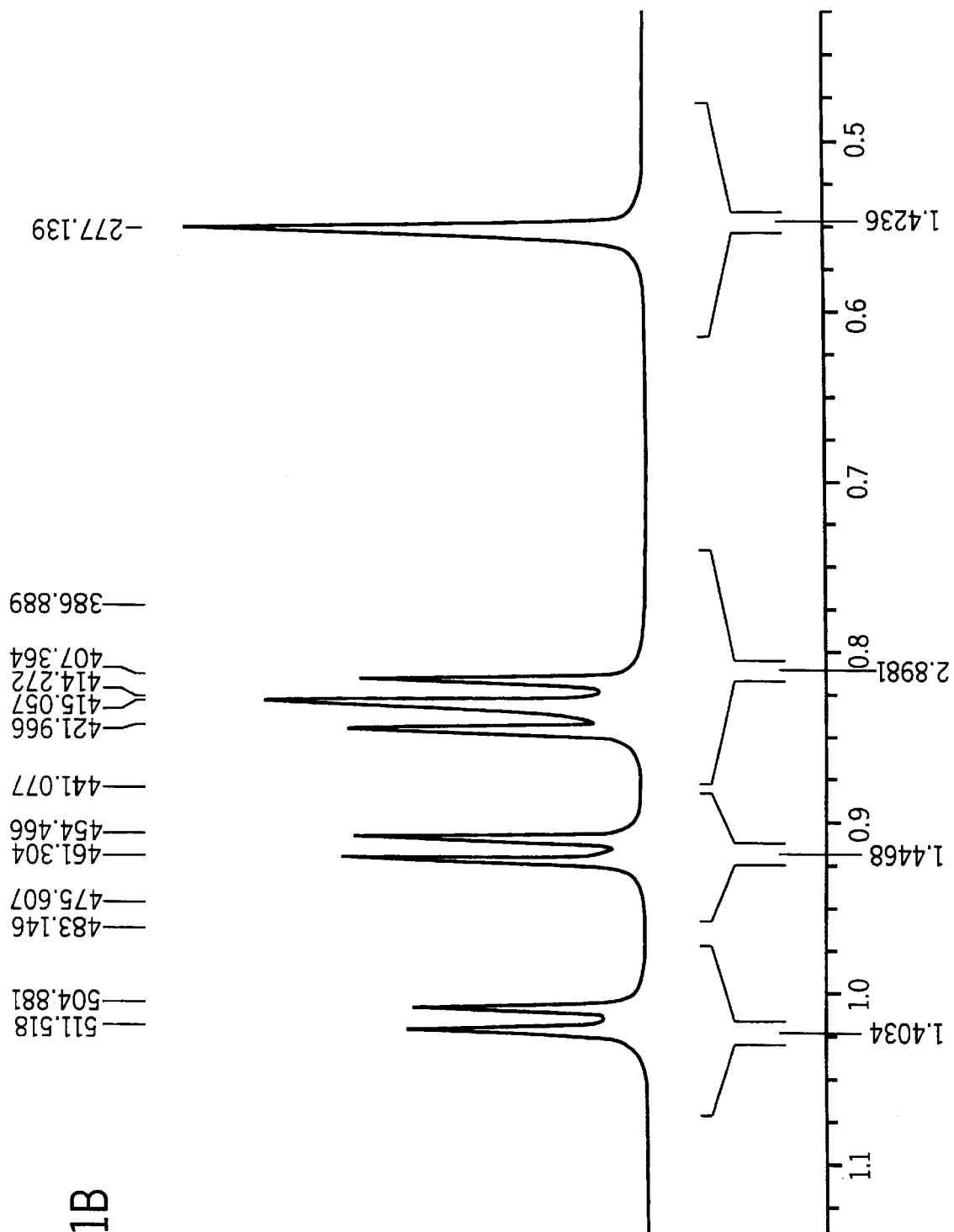
Figure 3C:
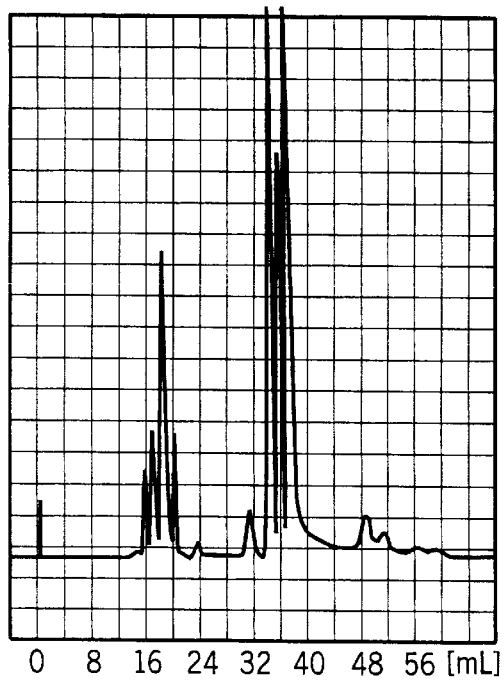

(b) These crystals of 1α-hydroxyvitamin $D_2$ (26.8 mg) were recrystallized with ethyl formate (0.5 mL) as described in Example 1(a) and the precipitated crystals (20 mg, 78%), m.p. 153–155° C., were observed under a microscope (FIGS. 4a, 4b) and analyzed by straight-phase HPLC (crystals: FIG. 2b; mother liquors: FIG. 3c), reverse-phase HPLC (FIG. 5b), and $^1$H NMR (FIGS. 1a, 1b).

EXAMPLE 2

Figure 3D:
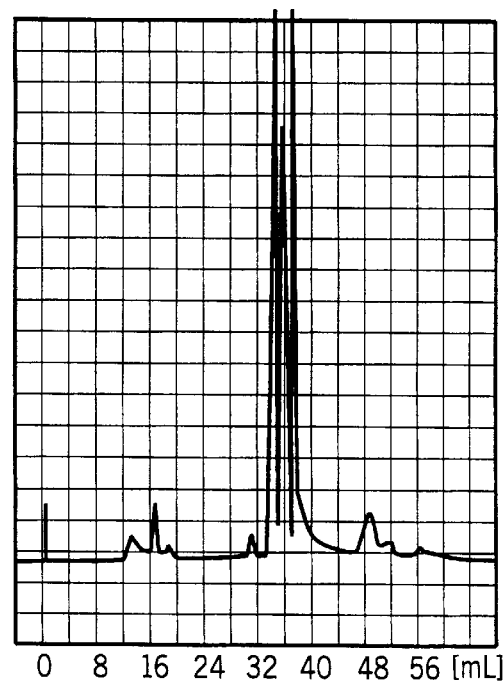
Figure 3E:
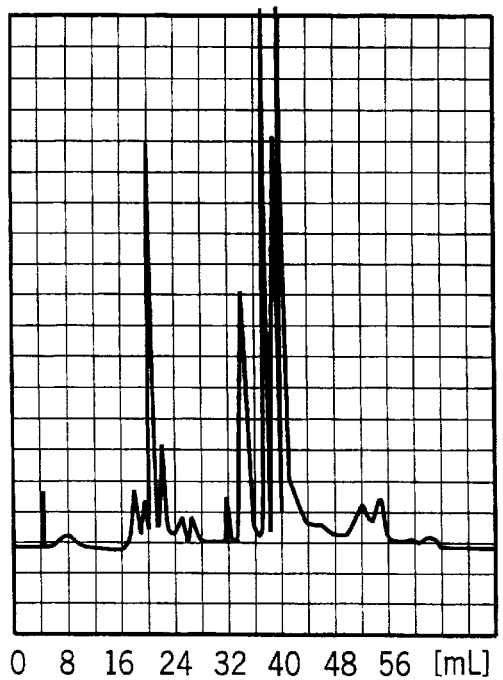

Crystallization from binary solvent system: ethyl acetate-petroleum ether (a) 1α-Hydroxyvitamin $D_2$ product (50 mg) to be purified was dissolved in boiling ethyl acetate (0.5 mL, Burdick&Jackson) under argon atmosphere and petroleum ether (1.5 mL, b.p. 35–60° C.; Aldrich) was added. The solution was left at room temperature (68° F.) for a few hours (1–3 hrs) and then in a refrigerator (35–45° F.) overnight (8–12 hrs). The precipitated crystals were filtered off, washed with a small volume of petroleum ether and dried. The yield of crystalline material was 32.5 mg (65%). HPLC profiles of crystals and mother liquor are shown in FIGS. 3d, 3e.

Figure 1C:
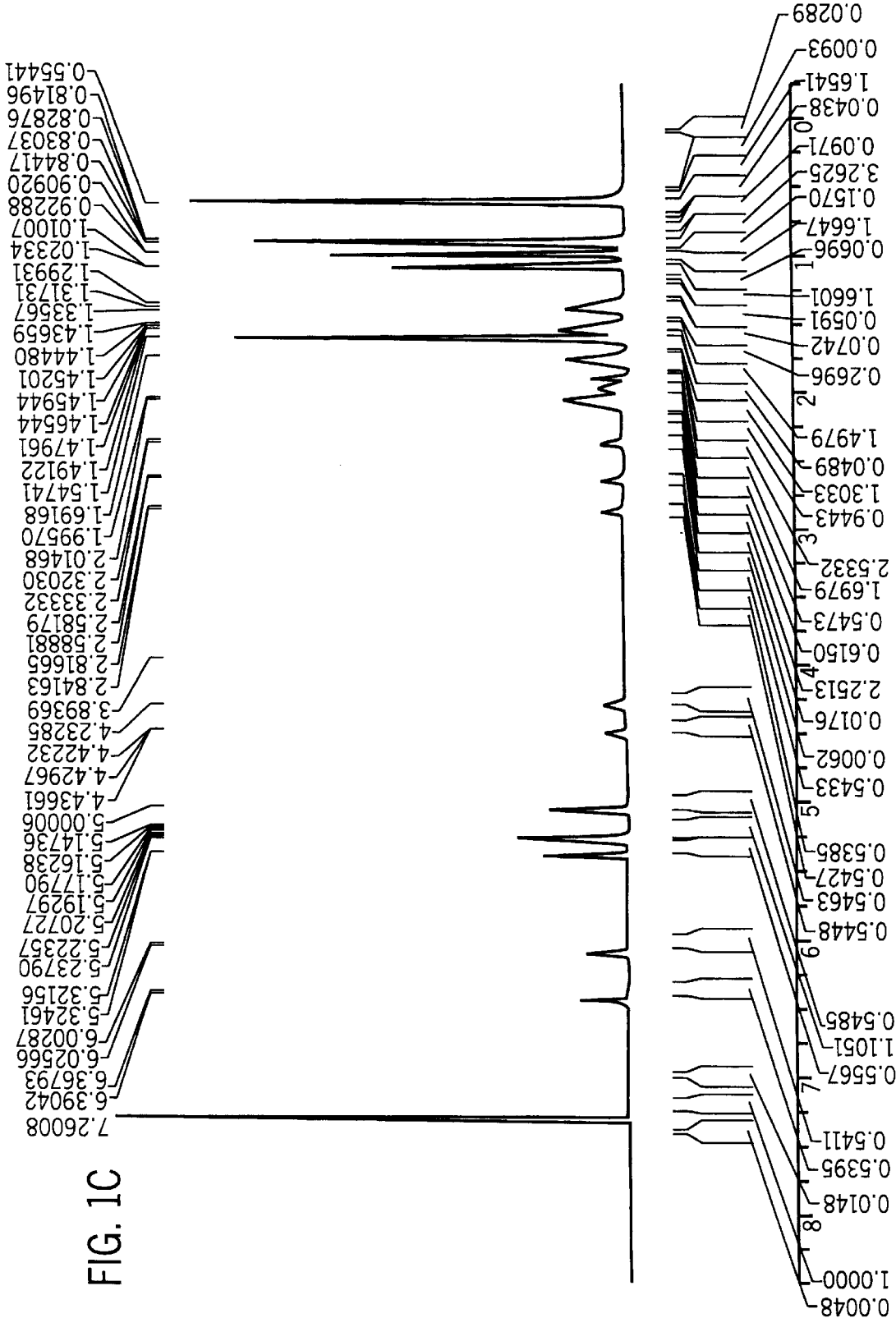
Figure 1D:
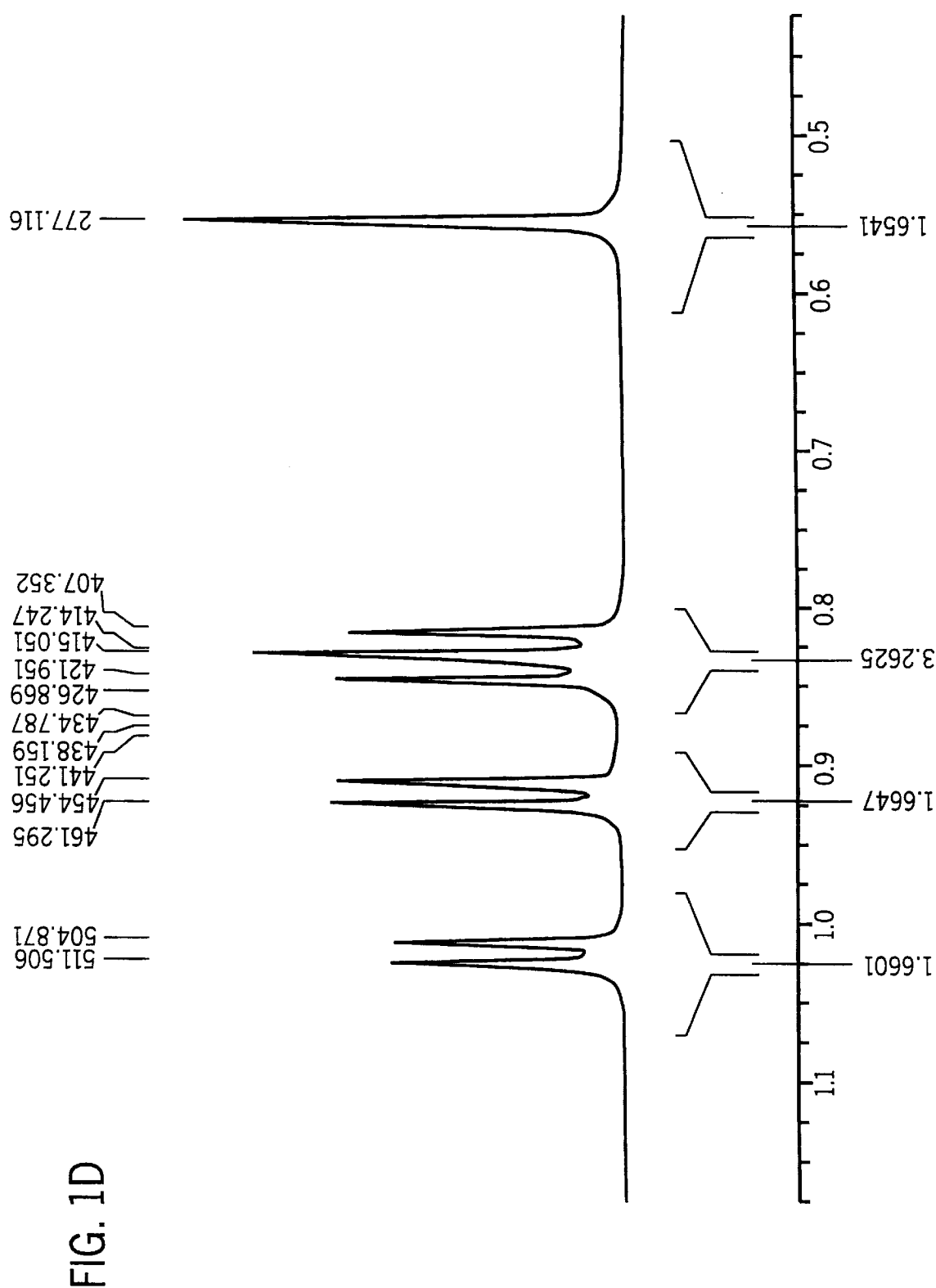
Figure 1E:
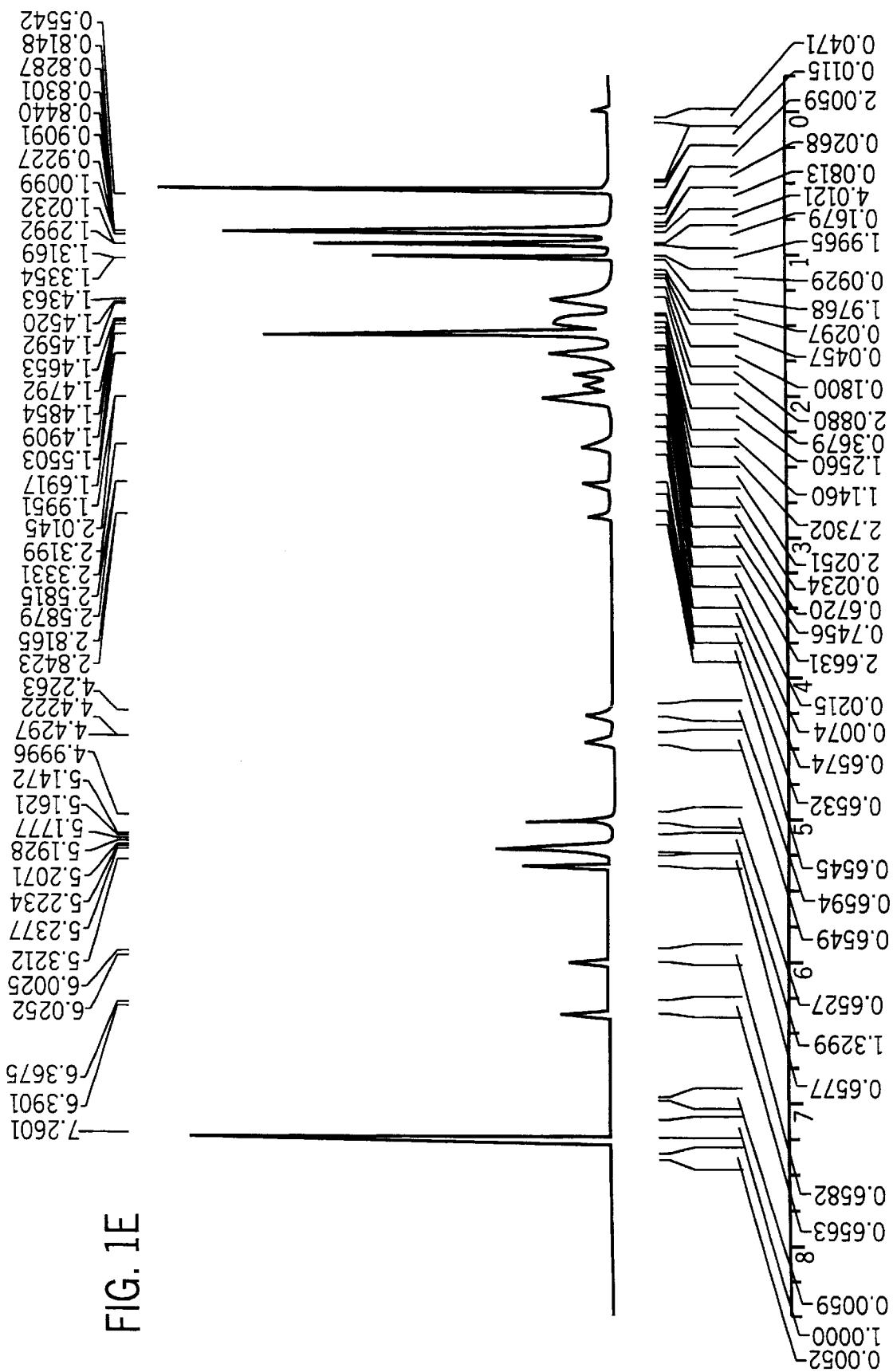
Figure 3F:
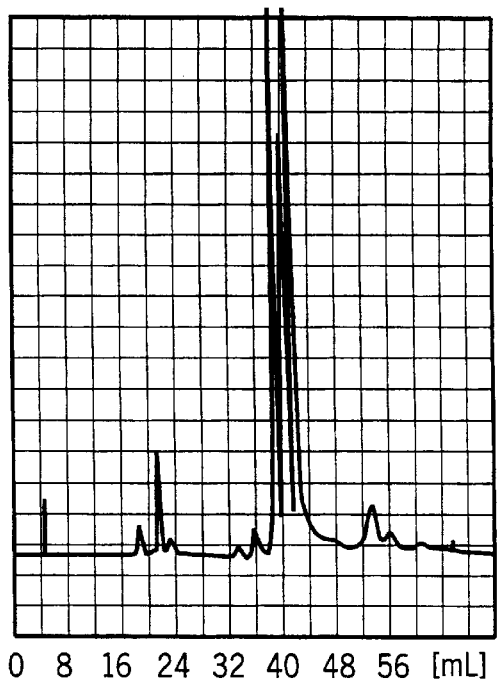

(b) These crystals of 1α-hydroxyvitamin $D_2$ (24.8 mg) were recrystallized with ethyl acetate (0.23 mL) and petroleum ether (0.69 mL) as described in Example 2(a) and the precipitated crystals (17 mg, 69%), m.p. 149.5–152.5° C., were observed under a microscope (FIGS. 4c, 4d) and analyzed by straight-phase HPLC (crystals: FIG. 2c; mother liquors: FIG. 3f), reverse-phase HPLC (FIG. 5c), and $^1$H NMR (FIGS. 1c, 1d).

EXAMPLE 3

Figure 3G:
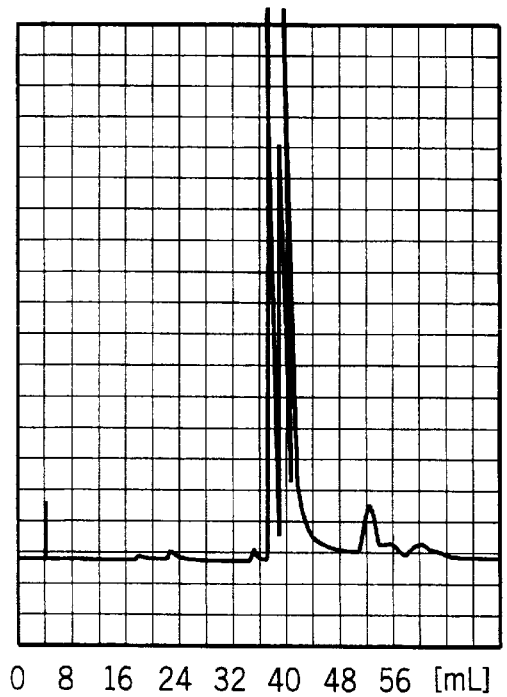
Figure 3H:
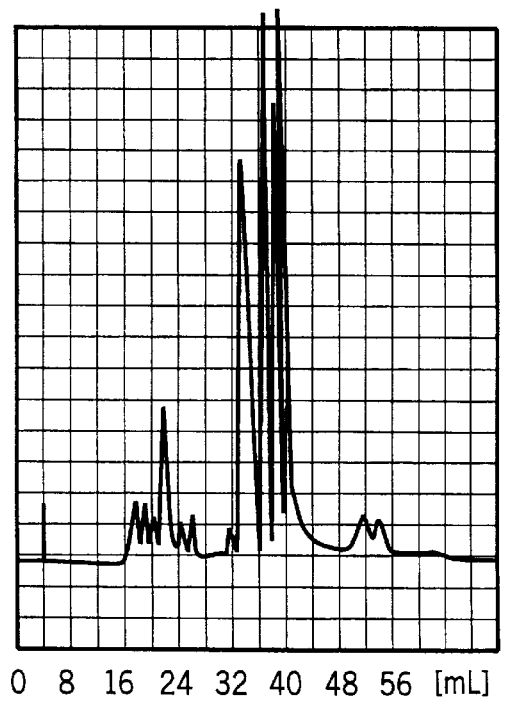

Crystallization from ternary solvent system: 2-propanol-hexane-petroleum ether (a) 1α-Hydroxyvitamin $D_2$ product (50 mg) to be purified was dissolved in boiling 2-propanol-hexane mixture (15:85; 0.6 mL; Burdick&Jackson) under argon atmosphere and petroleum ether (1.7 mL, b.p. 35–60° C.; Aldrich) was added. The solution was left at room temperature (68° F.) for a few hours (1–3 hrs) and then in a refrigerator (35–45° F.) overnight (8–12 hrs). The precipitated crystals were filtered off, washed with a small volume of petroleum ether and dried. The yield of crystalline material was 34.5 mg (69%). HPLC profiles of crystals and mother liquor are shown in FIGS. 3g, 3h.

Figure 1F:
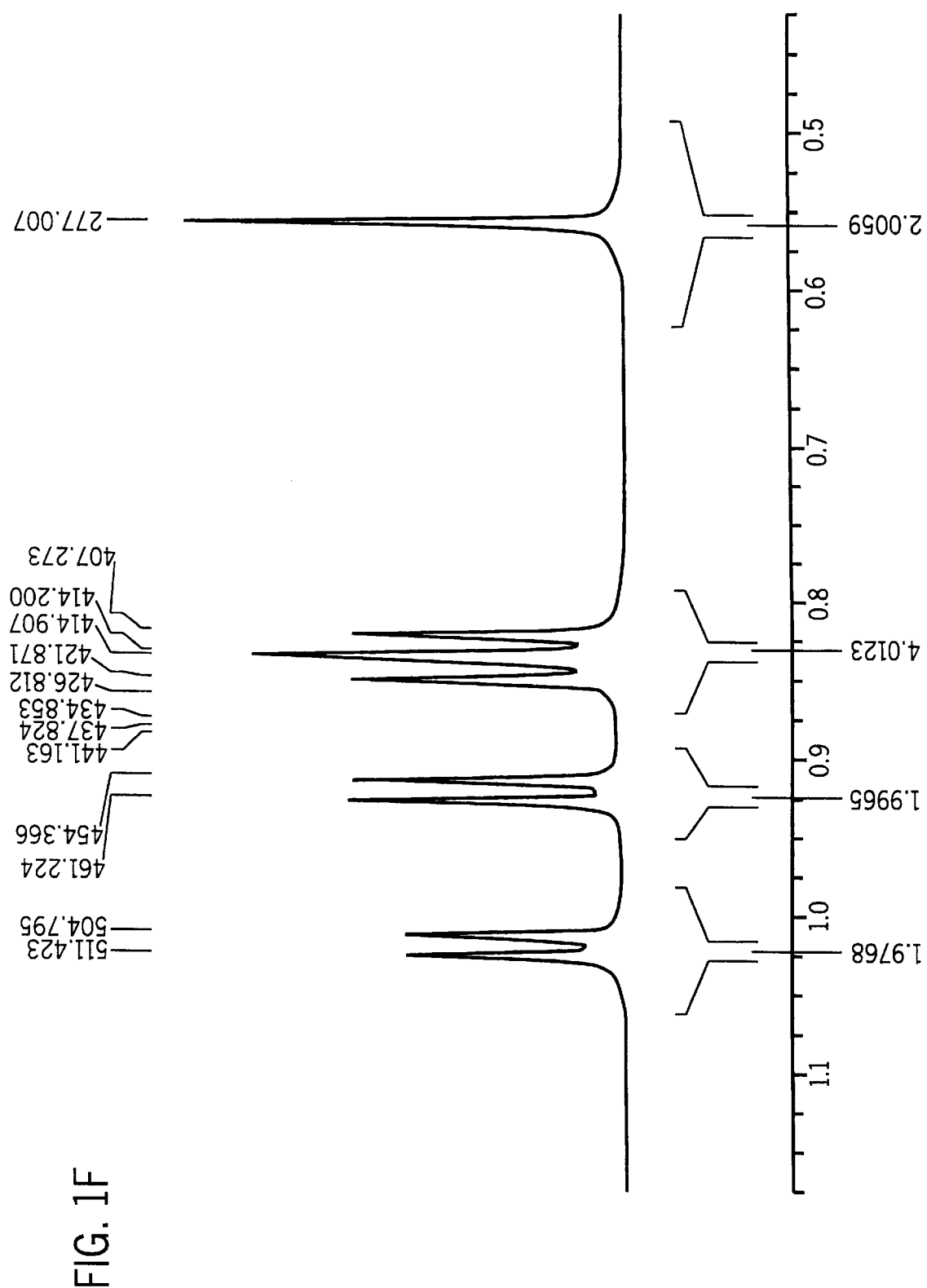
Figure 1G:
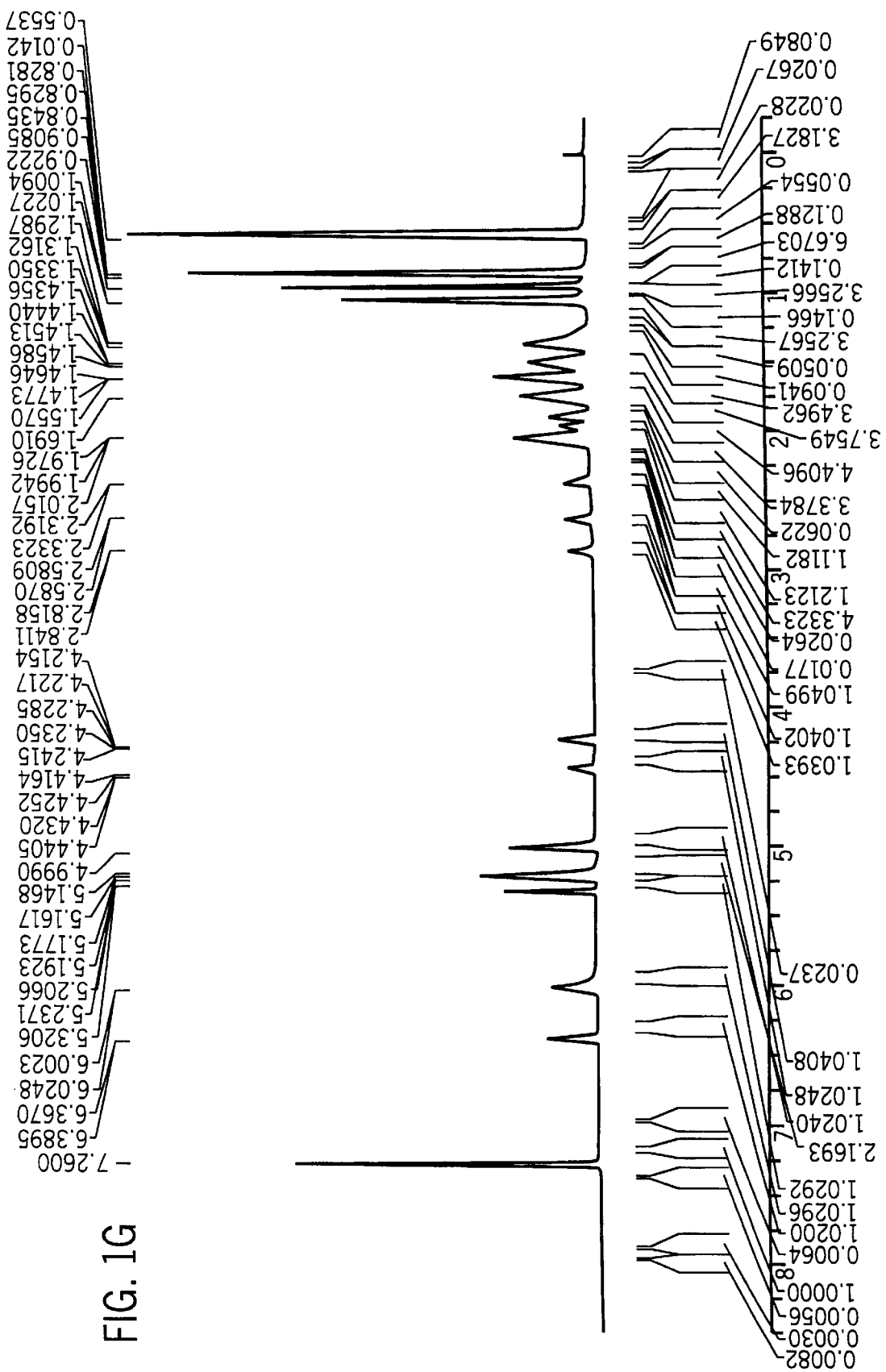
Figure 1H:
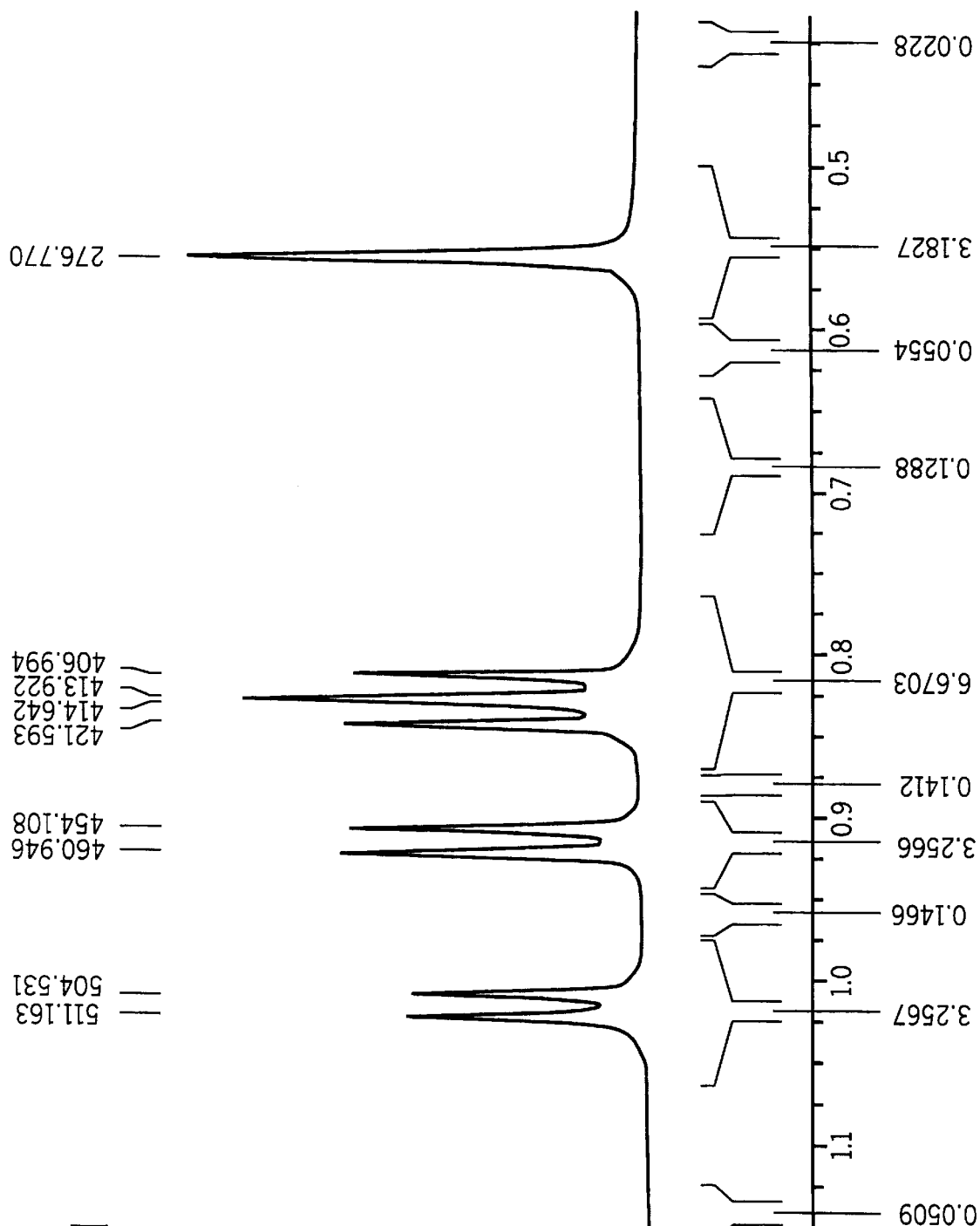
Figure 2D:
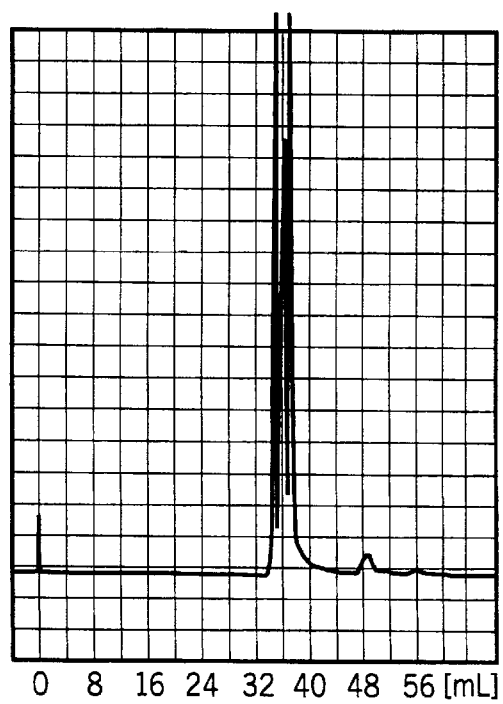
Figure 3I:
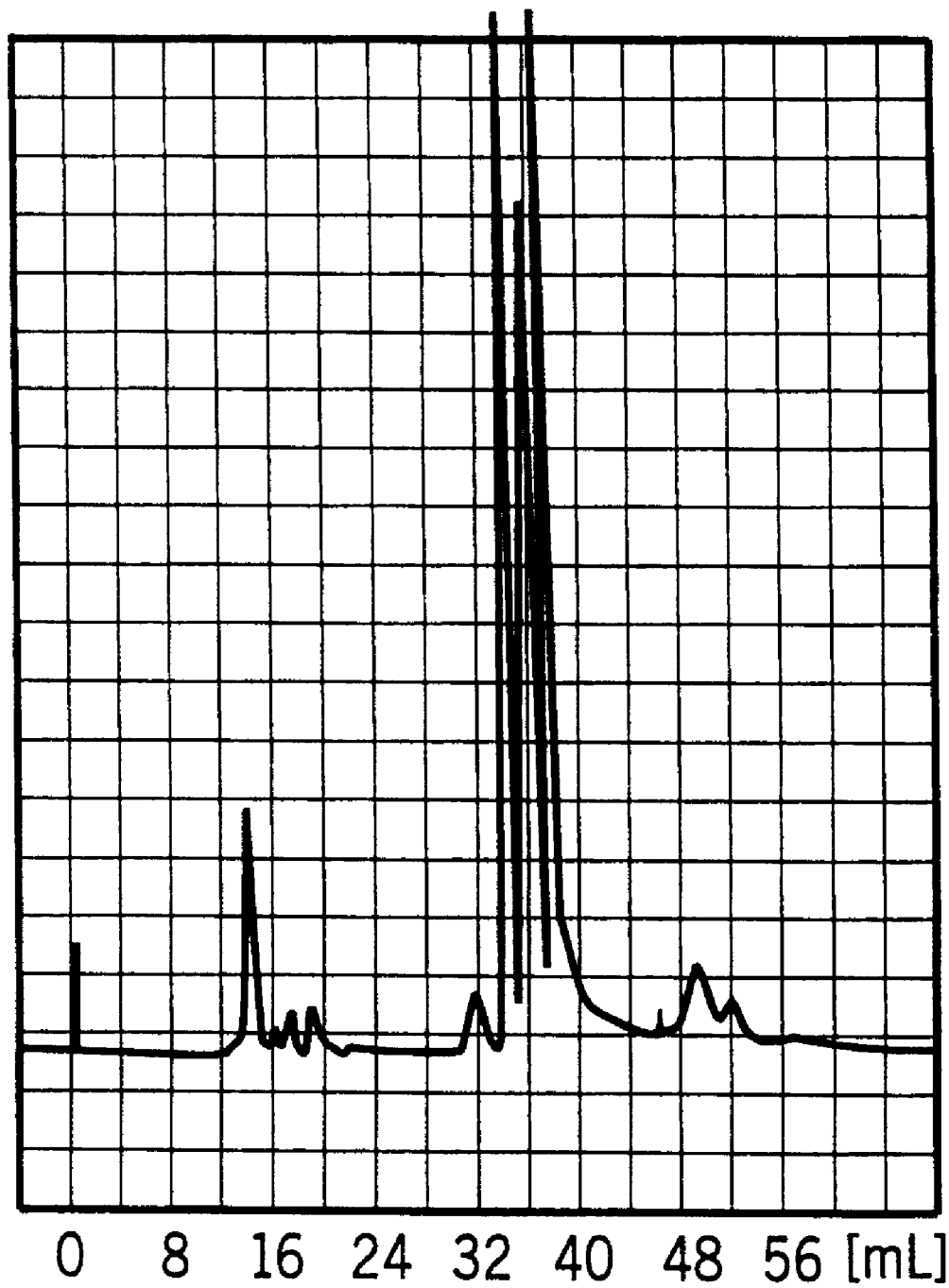
Figure 4A:
FIGS. 4a–4f are Microscope-magnified images of the crystals of 1α-hydroxyvitamin D$_2$ resulted after two crystallizations using the following solvent system: HCOOEt (FIG. 4a–40×, FIG. 4b–100×), AcOEt-petroleum ether (FIG. 4c–100×, FIG. 4d–400×) and iPrOH-hexane-petroleum ether (FIG. 4e–100×, FIG. 4f–400×).
Figure 4B:
Figure 4C:
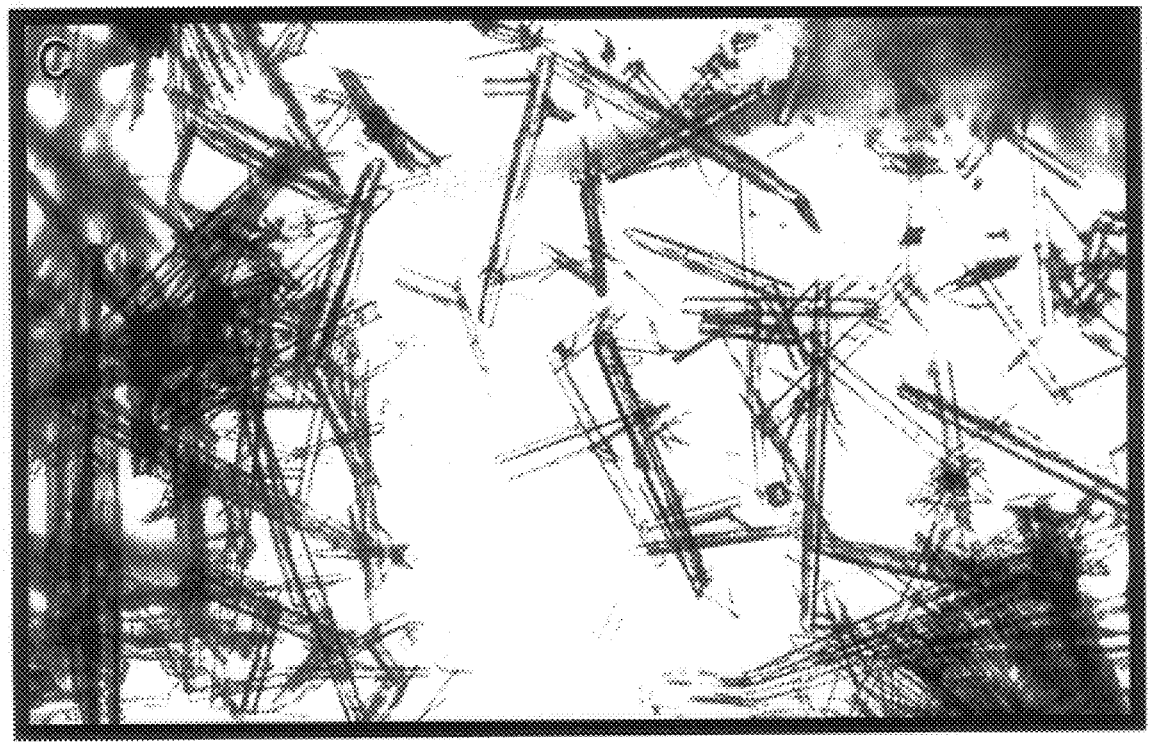
Figure 4D:
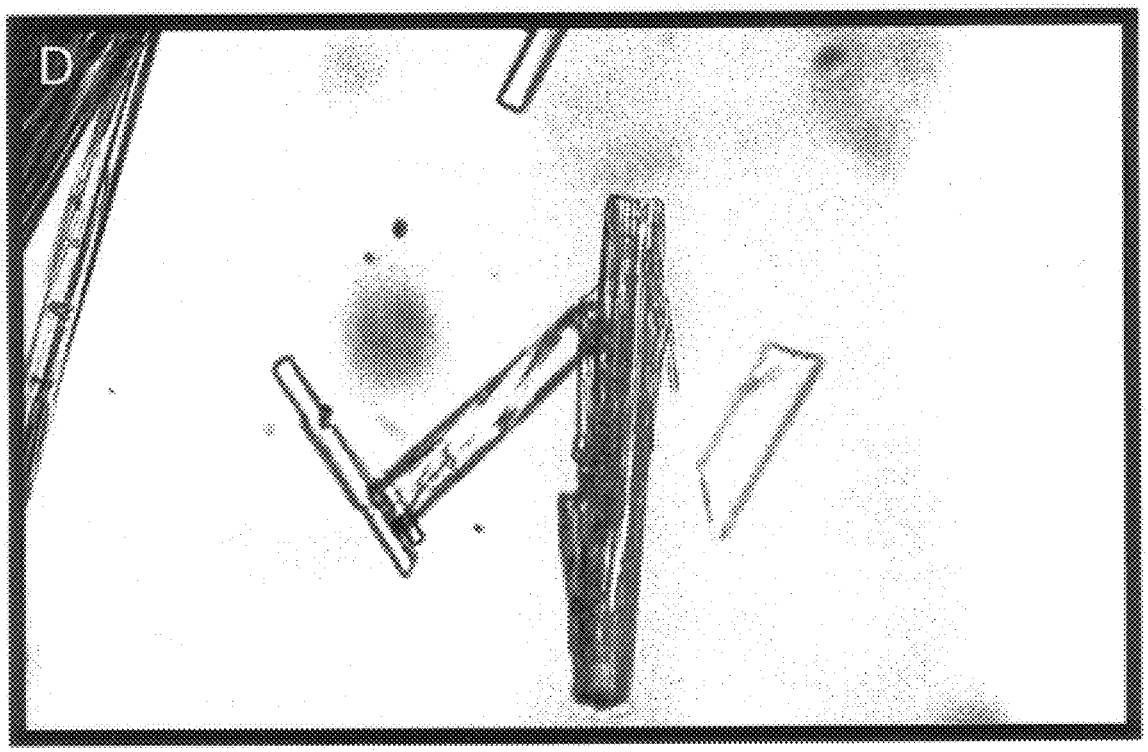
Figure 4E:
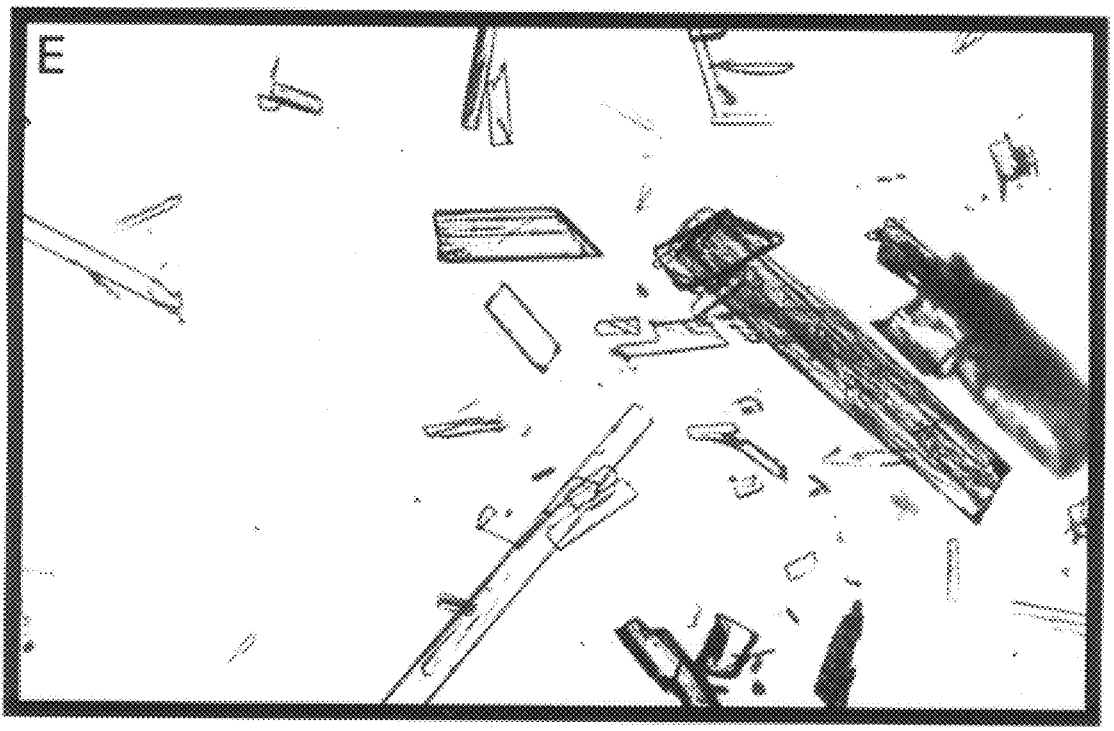
Figure 4F:
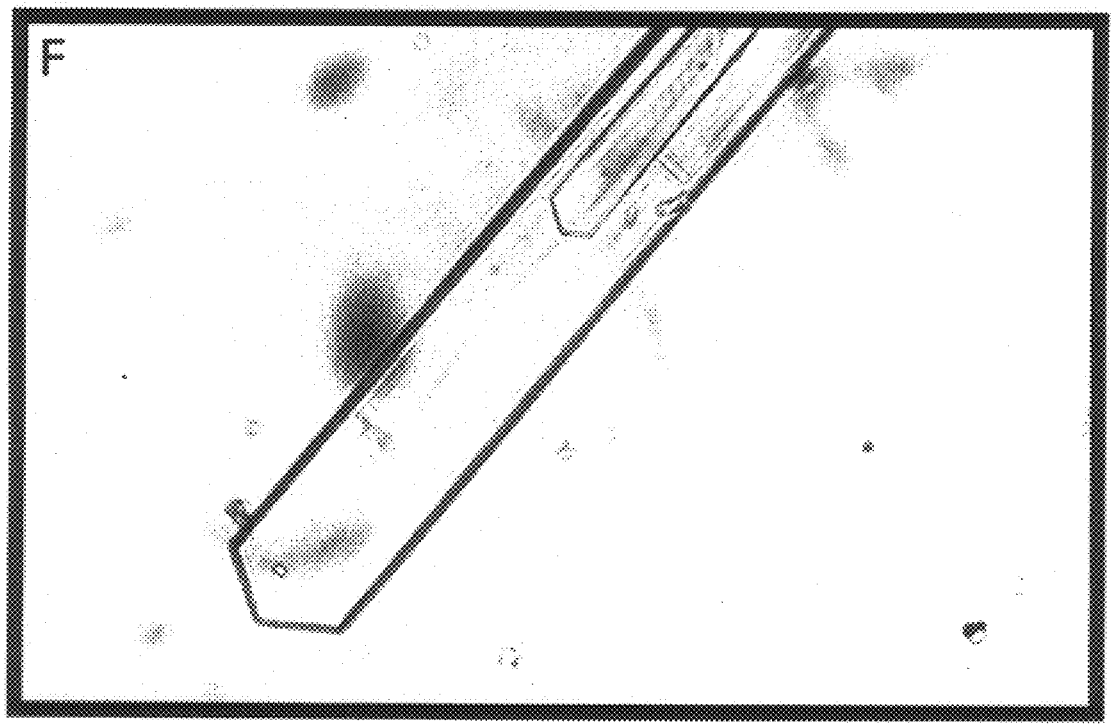

(b) These crystals of 1α-hydroxyvitamin $D_2$ (23.6 mg) were recrystallized with 2-propanol-hexane mixture (15:85; 0.15 mL) and petroleum ether (0.4 mL) as described in Example 3(a) and the precipitated crystals (15.6 mg, 66%), m.p. 154–156° C., were observed under a microscope (FIGS. 4e, 4f) and analyzed by straight-phase HPLC (crystals: FIG. 2d; mother liquors: FIG. 3i), reverse-phase HPLC (FIG. 5d), and $^1$H NMR (FIGS. 1a, 1f).

EXAMPLE 4

Experimental

A colorless prism-shaped crystal of dimensions 0.52× 0.44×0.38 mm was selected and designated as 98247 for structural analysis. Intensity data for this compound were collected using a Bruker SMART ccd area detector; (a) Data Collection: SMART Software Reference Manual (1994). Bruker-AXS, 6300 Enterprise Dr., Madison, Wis. 53719-1173, USA; (b) Data Reduction: SAINT Software Reference Manual (1995). Bruker-AXS, 6300 Enterprise Dr., Madison, Wis. 53719-1173, USA; mounted on a Bruker P4 goniometer using with graphite-monochromated Mo Kα radiation ($\lambda$=0.71073 §). The sample was cooled to 138° K. The intensity data, which nominally covered one and a half hemispheres of reciprocal space, were measured as a series of φ oscillation frames each of 0.4° for 30 sec/frame. The detector was operated in 512×512 mode and was positioned 5.00 cm from the sample. Coverage of unique data was 98.9% complete to 25.00 degrees in θ. Cell parameters were determined from a non-linear least squares fit of 3054 peaks in the range 3.0<θ<25.0°. The first 50 frames were repeated at the end of data collection and yielded a total of 140 peaks showing a variation of −0.15% during the data collection. A total of 6364 data were measured in the range 1.96<θ<28.20°. The data were corrected for absorption by the empirical method, G. M. Sheldrick (1996), SADABS, Program for Empirical Absorption Correction of Area Detector Data, University of Göttingen, Germany, giving minimum and maximum transmission factors of 0.744 and 0.970. The data were merged to form a set of 4597 independent data with R(int)=0.0320.

The Monoclinic space group C2 was determined by systematic absences and statistical tests and verified by subsequent refinement. The structure was solved by direct methods and refined by full-matrix least-squares methods on $F^2$, (a) G. M. Sheldrick (1994), SHELXTL Version 5 Reference Manual. Bruker-AXS, 6300 Enterprise Dr., Madison, Wis. 53719–1173, USA; (b) *International Tables for Crystallography*, Vol C, Tables 6.1.1.4, 4.2.6.8, and 4.2.4.2, Kluwer: Boston (1995). Hydrogen atom positions were initially determined by geometry and refined by a riding model. Non-hydrogen atoms were refined with anisotropic displacement parameters. A total of 281 parameters were refined against 3 restraints and 4597 data to give $wR(F^2)$= 0.1311 and S=0.938 for weights of $w=1/[\sigma^2 (F^2)+(0.0734 p)^2]$, where $P=[F_o^2+2F_c^2]/3$. The final R(F) was 0.0522 for the 3133 observed, [F>4σ(F)], data. The largest shift/s.u. was 0.001 in the final refinement cycle. The final difference map had maxima and minima of 0.317 and −0.295 e/§$^3$, respectively. The absolute structure was determined by refinement of the Flack parameter, H. D. Flack, *Acta Cryst.* A39, 876–881 (1983). The polar axis restraints were taken from Flack and Schwarzenbach, H. D. Flack and D. Schwarzenbach, *Acta Cryst.* A44, 499–506 (1988).

The displacement ellipsoids were drawn at the 50% probability level. Methyl group C(2) was disordered and modeled in two orientations with occupancies of 0.661(9) for the unprimed atom and 0.339(9) for the primed atom. Restraints were applied to the positional parameters of these atoms.

The three dimensional structure of 1α-hydroxyvitamin D$_2$ as defined by the following physical data and atomic positional parameters described and calculated herein is illustrated in FIG. 5.

TABLE 1

Crystal data and structure refinement for 98247.

| | |
|---|---|
| Identification code | 98247 |
| Empirical formula | C28 H45 O2 |
| Formula weight | 413.64 |
| Crystal system | Monoclinic |
| Space group | C2 |
| Unit cell dimensions | a = 23.952(4) Å α = 90° |
| | b = 6.8121(9) Å β = 119.579(2)° |
| | c = 17.994(2) Å γ = 90° |
| Volume | 2553.3(6) Å$^3$ |
| Z | 4 |
| Density (calculated) | 1.076 Mg/m$^3$ |
| Wavelength | 0.71073 Å |
| Temperature | 138(2)K |
| F(000) | 916 |
| Absorption coefficient | 0.065 mm$^{-1}$ |
| Absorption correction | Empirical |
| Max. and min. transmission | 0.970 and 0.744 |
| Theta range for data collection | 1.96 to 28.20°. |
| Reflections collected | 6364 |
| Independent reflections | 4597 [R(int) = 0.0320] |
| Data/restraints/parameters | 4597/3/281 |
| wR(F$^2$all data) | wR2 = 0.1311 |
| R(F obsd data) | R1 = 0.0522 |
| Goodness-of-fit on F$^2$ | 0.938 |
| Observed data [I > 2σ(I)] | 3.133 |
| Absolute structure parameter | 1.2(19) |
| Largest and mean shift/s.u. | 0.001 and 0.000 |
| Largest diff. peak and hole | 0.317 and −0.295 e/Å$^3$ |

TABLE 2

Atomic coordinates and equivalent isotropic displacement parameters for 98247. U(eq) is defined as one third of the trace of the orthogonalized U$_{ij}$ tensor.

| | x | y | z | U(eq) |
|---|---|---|---|---|
| O(1) | 0.54852(13) | 0.4364(3) | 0.97881(18) | 0.0713(8) |
| O(2) | 0.56423(10) | 1.0480(3) | 1.00431(14) | 0.0465(5) |

TABLE 2-continued

Atomic coordinates and equivalent isotropic displacement parameters for 98247. U(eq) is defined as one third of the trace of the orthogonalized U$_{ij}$ tensor.

| | x | y | z | U(eq) |
|---|---|---|---|---|
| C(1) | 0.57345(13) | 0.6257(4) | 0.98084(19) | 0.0355(6) |
| C(2) | 0.59343(13) | 0.7273(4) | 1.06595(17) | 0.0350(7) |
| C(3) | 0.61677(13) | 0.9353(4) | 1.06655(17) | 0.0349(6) |
| C(4) | 0.67265(13) | 0.9337(4) | 1.04799(16) | 0.0327(6) |
| C(5) | 0.65759(12) | 0.8180(4) | 0.96806(16) | 0.0281(6) |
| C(6) | 0.66835(12) | 0.8929(4) | 0.90804(16) | 0.0278(6) |
| C(7) | 0.64998(12) | 0.8085(4) | 0.82523(16) | 0.0290(6) |
| C(8) | 0.66086(12) | 0.8835(4) | 0.76415(16) | 0.0282(6) |
| C(9) | 0.69983(14) | 1.0672(4) | 0.77547(18) | 0.0364(7) |
| C(10) | 0.62870(12) | 0.6216(4) | 0.96228(17) | 0.0303(6) |
| C(11) | 0.74852(13) | 1.0392(4) | 0.74434(17) | 0.0343(6) |
| C(12) | 0.71843(13) | 0.9532(4) | 0.65447(16) | 0.0303(6) |
| C(13) | 0.68376(11) | 0.7601(4) | 0.64784(15) | 0.0266(6) |
| C(14) | 0.63338(12) | 0.8017(4) | 0.67657(16) | 0.0301(6) |
| C(15) | 0.59228(13) | 0.6150(5) | 0.65149(17) | 0.0385(7) |
| C(16) | 0.59231(14) | 0.5432(5) | 0.57008(18) | 0.0461(8) |
| C(17) | 0.63841(12) | 0.6810(4) | 0.55701(16) | 0.0307(6) |
| C(18) | 0.73112(12) | 0.6019(4) | 0.70394(17) | 0.0343(6) |
| C(19) | 0.64831(14) | 0.4570(4) | 0.94245(18) | 0.0391(7) |
| C(20) | 0.66588(13) | 0.5767(4) | 0.50566(17) | 0.0346(6) |
| C(21) | 0.71140(13) | 0.7081(4) | 0.49045(19) | 0.0408(7) |
| C(22) | 0.61101(13) | 0.5120(4) | 0.42223(17) | 0.0366(7) |
| C(23) | 0.59363(14) | 0.3296(5) | 0.39507(19) | 0.0430(7) |
| C(24) | 0.53471(15) | 0.2714(5) | 0.3132(2) | 0.0515(9) |
| C(25) | 0.5488(2) | 0.1850(5) | 0.2454(3) | 0.0788(13) |
| C(26) | 0.5847(2) | 0.3260(6) | 0.2199(2) | 0.0744(12) |
| C(27) | 0.5811(3) | −0.0047(7) | 0.2677(3) | 0.055(2) |
| C(27') | 0.5146(6) | −0.0003(16) | 0.2045(8) | 0.110(7) |
| C(28) | 0.49294(18) | 0.1351(6) | 0.3345(3) | 0.0771(12) |

TABLE 3

Bond lengths [Å] and angles [°] for 98247.

| O(1)-C(1) | 1.414(3) | C(10)-C(1)-C(2) | 110.7(2) |
|---|---|---|---|
| O(2)-C(3) | 1.427(3) | C(3)-C(2)-C(1) | 111.2(2) |
| C(1)-C(10) | 1.517(3) | O(2)-C(3)-C(2) | 108.5(2) |
| C(1)-C(2) | 1.526(4) | O(2)-C(3)-C(4) | 111.1(2) |
| C(2)-C(3) | 1.522(4) | C(2)-C(3)-C(4) | 110.4(2) |
| C(3)-C(4) | 1.531(4) | C(5)-C(4)-C(3) | 112.7(2) |
| C(4)-C(5) | 1.519(4) | C(6)-C(5)-C(10) | 124.0(2) |
| C(5)-C(6) | 1.330(3) | C(6)-C(5)-C(4) | 121.3(3) |
| C(5)-C(10) | 1.486(4) | C(10)-C(5)-C(4) | 114.7(2) |
| C(6)-C(7) | 1.448(3) | C(5)-C(6)-C(7) | 126.9(2) |
| C(7)-C(8) | 1.349(4) | C(8)-C(7)-C(6) | 127.3(2) |
| C(8)-C(14) | 1.484(3) | C(7)-C(8)-C(14) | 124.1(2) |
| C(8)-C(9) | 1.514(4) | C(7)-C(8)-C(9) | 123.9(2) |
| C(9)-C(11) | 1.535(4) | C(14)-C(8)-C(9) | 111.9(2) |
| C(10)-C(19) | 1.331(4) | C(8)-C(9)-C(11) | 112.2(2) |
| C(11)-C(12) | 1.525(3) | C(19)-C(10)-C(5) | 124.3(2) |
| C(12)-C(13) | 1.529(3) | C(19)-C(10)-C(1) | 122.4(2) |
| C(13)-C(18) | 1.529(3) | C(5)-C(10)-C(1) | 113.3(2) |
| C(13)-C(17) | 1.546(3) | C(12)-C(11)-C(9) | 112.8(2) |
| C(13)-C(14) | 1.556(3) | C(11)-C(12)-C(13) | 111.6(2) |
| C(14)-C(15) | 1.534(4) | C(12)-C(13)-C(18) | 111.0(2) |
| C(15)-C(16) | 1.545(4) | C(12)-C(13)-C(17) | 117.0(2) |
| C(16)-C(17) | 1.553(4) | C(18)-C(13)-C(17) | 111.0(2) |
| C(17)-C(20) | 1.546(3) | C(12)-C(13)-C(14) | 107.3(2) |
| C(20)-C(22) | 1.493(4) | C(18)-C(13)-C(14) | 110.7(2) |
| C(20)-C(21) | 1.536(4) | C(17)-C(13)-C(14) | 99.18(18) |
| C(22)-C(23) | 1.325(4) | C(8)-C(14)-C(15) | 120.5(2) |
| C(23)-C(24) | 1.505(4) | C(8)-C(14)-C(13) | 114.3(2) |

TABLE 3-continued

Bond lengths [Å] and angles [°] for 98247.

| | | | |
|---|---|---|---|
| C(24)-C(25) | 1.534(4) | C(15)-C(14)-C(13) | 104.0(2) |
| C(24)-C(28) | 1.545(4) | C(14)-C(15)-C(16) | 104.0(2) |
| C(25)-C(27) | 1.457(4) | C(15)-C(16)-C(17) | 106.6(2) |
| C(25)-C(27') | 1.486(6) | C(13)-C(17)-C(20) | 120.5(2) |
| C(25)-C(26) | 1.505(5) | C(13)-C(17)-C(16) | 103.4(2) |
| O(1)-C(1)-C(10) | 112.4(2) | C(20)-C(17)-C(16) | 110.9(2) |
| O(1)-C(1)-C(2) | 111.0(2) | C(22)-C(20)-C(21) | 110.1(2) |
| C(22)-C(20)-C(17) | 108.3(2) | C(27)-C(25)-C(27') | 58.1(6) |
| C(21)-C(20)-C(17) | 112.8(2) | C(27)-C(25)-C(26) | 110.1(4) |
| C(23)-C(22)-C(20) | 127.5(3) | C(27')-C(25)-C(26) | 130.4(6) |
| C(22)-C(23)-C(24) | 125.4(3) | C(27)-C(25)-C(24) | 114.6(4) |
| C(23)-C(24)-C(25) | 114.3(3) | C(27')-C(25)-C(24) | 115.9(5) |
| C(23)-C(24)-C(28) | 108.9(3) | C(26)-C(25)-C(24) | 112.4(3) |
| C(25)-C(24)-C(28) | 112.9(3) | | |

TABLE 4

Anisotropic displacement parameters (Å$^2$ × 10$^3$) for 98247. The anisotropic displacement factor exponent takes the form:
$-2\pi^2[h^2a^{*2}U_{11} + ... + 2hka^*b^*U_{12}]$

| | $U_{11}$ | $U_{22}$ | $U_{33}$ | $U_{23}$ | $U_{13}$ | $U_{12}$ |
|---|---|---|---|---|---|---|
| O(1) | 123(2) | 19(1) | 138(2) | −9(1) | 115(2) | −12(1) |
| O(2) | 58(1) | 34(1) | 68(1) | 17(1) | 46(1) | 21(1) |
| C(1) | 49(2) | 17(1) | 61(2) | 4(1) | 42(2) | 2(1) |
| C(2) | 42(2) | 30(2) | 47(2) | 12(1) | 33(1) | 9(1) |
| C(3) | 45(2) | 32(2) | 39(2) | 6(1) | 28(1) | 7(1) |
| C(4) | 39(2) | 31(2) | 36(1) | 5(1) | 24(1) | 4(1) |
| C(5) | 29(1) | 24(1) | 34(1) | 4(1) | 18(1) | 6(1) |
| C(6) | 25(1) | 25(1) | 35(1) | 1(1) | 17(1) | 0(1) |
| C(7) | 28(1) | 26(1) | 35(1) | 2(1) | 16(1) | 0(1) |
| C(8) | 27(1) | 25(1) | 34(1) | 2(1) | 16(1) | 2(1) |
| C(9) | 45(2) | 30(2) | 40(2) | −1(1) | 25(1) | −8(1) |
| C(10) | 38(2) | 21(1) | 41(2) | 9(1) | 27(1) | 8(1) |
| C(11) | 41(2) | 28(2) | 40(2) | 0(1) | 25(1) | −9(1) |
| C(12) | 33(1) | 29(1) | 33(1) | 5(1) | 20(1) | 2(1) |
| C(13) | 23(1) | 28(2) | 32(1) | 5(1) | 16(1) | 2(1) |
| C(14) | 26(1) | 33(2) | 33(1) | 3(1) | 16(1) | 1(1) |
| C(15) | 30(1) | 50(2) | 42(2) | −13(1) | 23(1) | −12(1) |
| C(16) | 36(2) | 62(2) | 46(2) | −15(2) | 25(1) | −13(2) |
| C(17) | 25(1) | 38(2) | 31(1) | −2(1) | 15(1) | 1(1) |
| C(18) | 35(2) | 28(2) | 43(2) | 5(1) | 21(1) | 2(1) |
| C(19) | 45(2) | 37(2) | 44(2) | 10(1) | 29(2) | 9(1) |
| C(20) | 37(2) | 33(2) | 40(2) | −3(1) | 23(1) | −1(1) |
| C(21) | 44(2) | 41(2) | 51(2) | −10(1) | 34(1) | −7(1) |
| C(22) | 43(2) | 32(2) | 42(2) | −1(1) | 26(1) | −1(1) |
| C(23) | 46(2) | 42(2) | 53(2) | −5(2) | 34(2) | −4(2) |
| C(24) | 55(2) | 52(2) | 65(2) | −31(2) | 43(2) | −24(2) |
| C(25) | 103(3) | 67(3) | 105(3) | 81(3) | 81(3) | −38(2) |
| C(26) | 100(3) | 76(3) | 82(3) | −27(2) | 71(2) | −28(2) |
| C(27) | 84(4) | 43(3) | 61(4) | 1(2) | 54(3) | 6(3) |
| C(27') | 87(11) | 166(17) | 81(10) | −77(10) | 45(9) | −31(10) |
| C(28) | 77(3) | 79(3) | 106(3) | −40(2) | 70(2) | −40(2) |

TABLE 5

Hydrogen coordinates and isotropic displacement parameters for 98247.

| | x | y | z | U(eq) |
|---|---|---|---|---|
| H(1A) | 0.5187 | 0.4364 | 0.9914 | 0.107 |
| H(1B) | 0.5682 | 0.3243 | 1.0063 | 0.107 |
| H(2A) | 0.5737 | 1.1693 | 0.9770 | 0.070 |
| H(2B) | 0.5319 | 1.0320 | 1.0104 | 0.070 |
| H(1) | 0.5382 | 0.7054 | 0.9350 | 0.043 |
| H(2A) | 0.5564 | 0.7314 | 1.0761 | 0.042 |
| H(2B) | 0.6281 | 0.6510 | 1.1128 | 0.042 |
| H(3) | 0.6318 | 0.9944 | 1.1242 | 0.042 |
| H(4A) | 0.6833 | 1.0705 | 1.0412 | 0.039 |
| H(4B) | 0.7108 | 0.8758 | 1.0974 | 0.039 |
| H(6) | 0.6904 | 1.0149 | 0.9208 | 0.033 |
| H(7) | 0.6278 | 0.6868 | 0.8125 | 0.035 |
| H(9A) | 0.7230 | 1.1039 | 0.8367 | 0.044 |
| H(9B) | 0.6704 | 1.1762 | 0.7433 | 0.044 |
| H(11A) | 0.7681 | 1.1676 | 0.7450 | 0.041 |
| H(11B) | 0.7832 | 0.9509 | 0.7844 | 0.041 |
| H(12A) | 0.7524 | 0.9301 | 0.6393 | 0.036 |
| H(12B) | 0.6875 | 1.0486 | 0.6132 | 0.036 |
| H(14) | 0.6048 | 0.9068 | 0.6375 | 0.036 |
| H(15A) | 0.5481 | 0.6445 | 0.6395 | 0.046 |
| H(15B) | 0.6114 | 0.5154 | 0.6974 | 0.046 |
| H(16A) | 0.5485 | 0.5500 | 0.5202 | 0.055 |
| H(16B) | 0.6075 | 0.4056 | 0.5772 | 0.055 |
| H(17) | 0.6123 | 0.7945 | 0.5218 | 0.037 |
| H(18A) | 0.7505 | 0.6404 | 0.7641 | 0.051 |
| H(18B) | 0.7084 | 0.4770 | 0.6951 | 0.051 |
| H(18C) | 0.7648 | 0.5868 | 0.6885 | 0.051 |
| H(19A) | 0.6649 | 0.3664 | 0.9910 | 0.059 |
| H(19B) | 0.6121 | 0.3958 | 0.8927 | 0.059 |
| H(19C) | 0.6823 | 0.4877 | 0.9290 | 0.059 |
| H(20) | 0.6901 | 0.4578 | 0.5382 | 0.042 |
| H(21A) | 0.7217 | 0.6437 | 0.4500 | 0.061 |
| H(21B) | 0.6905 | 0.8343 | 0.4669 | 0.061 |
| H(21C) | 0.7510 | 0.7300 | 0.5447 | 0.061 |
| H(22) | 0.5856 | 0.6132 | 0.3842 | 0.044 |
| H(23) | 0.6206 | 0.2269 | 0.4302 | 0.052 |
| H(24) | 0.5093 | 0.3940 | 0.2883 | 0.062 |
| H(25) | 0.5062 | 0.1628 | 0.1932 | 0.095 |
| H(25') | 0.5869 | 0.1178 | 0.2864 | 0.095 |
| H(26A) | 0.5891 | 0.2695 | 0.1730 | 0.112 |
| H(26B) | 0.5611 | 0.4500 | 0.2013 | 0.112 |
| H(26C) | 0.6274 | 0.3502 | 0.2689 | 0.112 |
| H(27A) | 0.5881 | −0.0496 | 0.2212 | 0.083 |
| H(27B) | 0.6225 | 0.0083 | 0.3202 | 0.083 |
| H(27C) | 0.5544 | −0.1002 | 0.2767 | 0.083 |
| H(27D) | 0.5271 | −0.0434 | 0.1627 | 0.164 |
| H(27E) | 0.5261 | −0.1018 | 0.2482 | 0.164 |
| H(27F) | 0.4682 | 0.0222 | 0.1754 | 0.164 |
| H(28A) | 0.4777 | 0.2077 | 0.3681 | 0.116 |
| H(28B) | 0.4561 | 0.0889 | 0.2813 | 0.116 |
| H(28C) | 0.5186 | 0.0224 | 0.3676 | 0.116 |

TABLE 6

Torsion angles [°] for 98247.

| | | | |
|---|---|---|---|
| O(1)-C(1)-C(2)-C(3) | −176.8(2) | C(12)-C(13)-C(14)-C(8) | −57.5(3) |
| C(10)-C(1)-C(2)-C(3) | 57.6(3) | C(18)-C(13)-C(14)-C(8) | 63.7(3) |
| C(1)-C(2)-C(3)-O(2) | 64.8(3) | C(17)-C(13)-C(14)-C(8) | −179.7(2) |
| C(1)-C(2)-C(3)-C(4) | −57.2(3) | C(12)-C(13)-C(14)-C(15) | 169.2(2) |
| O(2)-C(3)-C(4)-C(5) | −69.0(3) | C(18)-C(13)-C(14)-C(15) | −69.6(2) |
| C(2)-C(3)-C(4)-C(5) | 51.4(3) | C(17)-C(13)-C(14)-C(15) | 47.0(2) |
| C(3)-C(4)-C(5)-C(6) | 130.8(3) | C(8)-C(14)-C(15)-C(16) | −162.1(2) |
| C(3)-C(4)-C(5)-C(10) | −47.5(3) | C(13)-C(14)-C(15)-C(16) | −32.4(3) |
| C(10)-C(5)-C(6)-C(7) | 5.3(4) | C(14)-C(15)-C(16)-C(17) | 5.0(3) |
| C(4)-C(5)-C(6)-C(7) | −172.8(2) | C(12)-C(13)-C(17)-C(20) | 77.7(3) |
| C(5)-C(6)-C(7)-C(8) | −179.8(3) | C(18)-C(13)-C(17)-C(20) | −51.0(3) |
| C(6)-C(7)-C(8)-C(14) | −171.8(2) | C(14)-C(13)-C(17)-C(20) | −167.4(2) |
| C(6)-C(7)-C(8)-C(9) | 4.9(4) | C(12)-C(13)-C(17)-C(16) | −157.8(2) |
| C(7)-C(8)-C(9)-C(11) | 133.3(3) | C(18)-C(13)-C(17)-C(16) | 73.5(3) |
| C(14)-C(8)-C(9)-C(11) | −49.6(3) | C(14)-C(13)-C(17)-C(16) | −42.9(3) |
| C(6)-C(5)-C(10)-C(19) | 49.5(4) | C(15)-C(16)-C(17)-C(13) | 24.2(3) |
| C(4)-C(5)-C(10)-C(19) | −132.3(3) | C(15)-C(16)-C(17)-C(20) | 154.8(2) |
| C(6)-C(5)-C(10)-C(1) | −130.1(3) | C(13)-C(17)-C(20)-C(22) | 178.3(2) |
| C(4)-C(5)-C(10)-C(1) | 48.1(3) | C(16)-C(17)-C(20)-C(22) | 57.5(3) |
| O(1)-C(1)-C(10)-C(19) | 3.0(4) | C(13)-C(17)-C(20)-C(21) | −59.6(3) |
| C(2)-C(1)-C(10)-C(19) | 127.8(3) | C(16)-C(17)-C(20)-C(21) | 179.5(2) |
| O(1)-C(1)-C(10)-C(5) | −177.3(2) | C(21)-C(20)-C(22)-C(23) | 121.8(3) |
| C(2)-C(1)-C(10)-C(5) | −52.5(3) | C(17)-C(20)-C(22)-C(23) | −114.4(3) |
| C(8)-C(9)-C(11)-C(12) | 50.4(3) | C(20)-C(22)-C(23)-C(24) | 174.8(3) |
| C(9)-C(11)-C(12)-C(13) | −55.2(3) | C(22)-C(23)-C(24)-C(25) | 110.7(4) |
| C(11)-C(12)-C(13)-C(18) | −64.9(3) | C(22)-C(23)-C(24)-C(28) | −121.9(3) |
| C(11)-C(12)-C(13)-C(17) | 166.5(2) | C(23)-C(24)-C(25)-C(27) | 67.2(4) |
| C(11)-C(12)-C(13)-C(14) | 56.2(3) | C(28)-C(24)-C(25)-C(27) | −58.1(5) |
| C(7)-C(8)-C(14)-C(15) | −3.1(4) | C(23)-C(24)-C(25)-C(27') | 132.1(8) |
| C(9)-C(8)-C(14)-C(15) | 179.9(2) | C(28)-C(24)-C(25)-C(27') | 6.8(8) |
| C(7)-C(8)-C(14)-C(13) | −128.0(3) | C(23)-C(24)-C(25)-C(26) | −59.5(5) |
| C(9)-C(8)-C(14)-C(13) | 54.9(3) | C(28)-C(24)-C(25)-C(26) | 175.2(4) |

TABLE 7

Hydrogen bonds for 98247[Å and °].

| D-H...A | d(D-H) | d(H...A) | d(D...A) | <(DHA) |
|---|---|---|---|---|
| O(1)-H(1A)...O(1)#1 | 0.85 | 1.93 | 2.781(4) | 179.4 |
| O(1)-H(1B)...O(2)#2 | 0.91 | 1.88 | 2.679(3) | 145.5 |
| O(2)-H(2A)...O(1)#3 | 1.04 | 1.92 | 2.679(3) | 126.8 |
| O(2)-H(2B)...O(2)#1 | 0.84 | 2.19 | 3.004(4) | 163.7 |

Symmetry transformations used to generate equivalent atoms:
1 −x + 1, y, −z + 2 #2x, y − 1, z #3 x, y + 1, z

What is claimed is:

1. A method of purifying 1α-hydroxyvitamin $D_2$, comprising the steps of:
   (a) boiling a solvent consisting essentially of ethyl formate under inert atmosphere;
   (b) dissolving a product containing 1α-hydroxyvitamin $D_2$ to be purified in said solvent;
   (c) cooling said solvent and dissolved product below ambient temperature for a sufficient amount of time to form a precipitate of 1α-hydroxyvitamin $D_2$ crystals; and
   (d) recovering the 1α-hydroxyvitamin $D_2$ crystals having a molecular packing arrangement defined by space group C2 and unit cell dimensions a=23.9A°, b=6.8A°, c=17.9A°, α=90°, β=119.5° and γ=90°.

2. The method of claim 1 wherein said solvent and dissolved product is allowed to cool to ambient temperature prior to cooling below ambient temperature.

3. The method of claim 1 wherein said inert atmosphere is an argon atmosphere.

4. The method of claim 1 wherein said solvent and dissolved product is cooled to between about 35° F. to about 45° F.

5. The method of claim 1 wherein the step of recovering comprises filtering.

6. The method of claim 1 wherein steps (a) through (d) are repeated using the recovered crystals from step (d) as the product in step (b).

7. A method of purifying 1α-hydroxyvitamin $D_2$, comprising the steps of:
   (a) boiling a solvent consisting essentially of ethyl acetate under inert atmosphere;
   (b) dissolving a product containing 1α-hydroxyvitamin $D_2$ to be purified in said solvent;
   (c) adding petroleum ether to said solvent after dissolving said product in said solvent;
   (d) cooling said solvent and dissolved product below ambient temperature for a sufficient amount of time to form a precipitate of 1α-hydroxyvitamin $D_2$ crystals; and
   (e) recovering the 1α-hydroxyvitamin $D_2$ crystals having a molecular packing arrangement defined by space group C2 and unit cell dimensions a=23.9A°, b=6.8A°, c=17.9A°, α=90°, β=119.5° and γ=90°.

8. The method of claim 7 wherein said solvent and dissolved product is allowed to cool to ambient temperature prior to cooling below ambient temperature.

9. The method of claim 7 wherein said inert atmosphere is an argon atmosphere.

10. The method of claim 7 wherein said solvent and dissolved product is cooled to between about 35° F. to about 45° F.

11. The method of claim 7 wherein the step of recovering comprises filtering.

12. The method of claim 7 herein steps (a) through (e) are repeated using the recovered crystals from step (e) as the product in step (b).

13. A method of purifying 1α-hydroxyvitamin $D_2$, comprising the steps of:
(a) boiling a solvent consisting essentially of 2-propanol-hexane mixture under inert atmosphere;
(b) dissolving a product containing 1α-hydroxyvitamin $D_2$ to be purified in said solvent;
(c) adding petroleum ether to said solvent after dissolving said product in said solvent;
(d) cooling said solvent and dissolved product below ambient temperature for a sufficient amount of time to form a precipitate of 1α-hydroxyvitamin $D_2$ crystals; and
(e) recovering the 1α-hydroxyvitamin $D_2$ crystals having a molecular packing arrangement defined by space group C2 and unit cell dimensions a=23.9A°, b=6.8A°, c=17.9A°, α=90°, β=119.5° and γ=90°.

14. The method of claim 13 wherein said solvent and dissolved product is allowed to cool to ambient temperature prior to cooling below ambient temperature.

15. The method of claim 13 wherein said inert atmosphere is an argon atmosphere.

16. The method of claim 13 wherein said solvent and dissolved product is cooled to between about 35° F. to about 45° F.

17. The method of claim 13 wherein the step of recovering comprises filtering.

18. The method of claim 13 wherein steps (a) through (e) are repeated using the recovered crystals from step (e) as the product in step (b).

* * * * *